US012781251B2

(12) United States Patent
Nobbs et al.

(10) Patent No.: US 12,781,251 B2
(45) Date of Patent: Nov. 3, 2026

(54) SYSTEMS AND METHODS OF MAKING OIL FROM MICROORGANISMS

(71) Applicant: ZERO ACRE FARMS INC., San Mateo, CA (US)

(72) Inventors: Jeff Nobbs, San Francisco, CA (US); Jay D. Keasling, Berkeley, CA (US); Stephen B. Del Cardayre, Belmont, CA (US)

(73) Assignee: Cemvita Factory, Inc., Houston, TX (US)

( * ) Notice: Subject to any disclaimer, the term of this patent is extended or adjusted under 35 U.S.C. 154(b) by 428 days.

(21) Appl. No.: 18/452,040

(22) Filed: Aug. 18, 2023

(65) Prior Publication Data

US 2024/0060101 A1 Feb. 22, 2024

Related U.S. Application Data

(63) Continuation of application No. PCT/US2022/017064, filed on Feb. 18, 2022.

(60) Provisional application No. 63/150,937, filed on Feb. 18, 2021.

(51) Int. Cl.
*C12P 7/6463* (2022.01)
*C12N 1/16* (2026.01)

(52) U.S. Cl.
CPC .............. *C12P 7/6463* (2013.01); *C12N 1/16* (2013.01); *C12N 2500/30* (2013.01)

(58) Field of Classification Search
CPC ...... C12P 7/6463; C12P 2203/00; C12N 1/16; C12N 2500/30; C12R 2001/645; C12R 2001/73; A23D 9/02; C11B 1/10; C11B 3/16; C11B 1/025; Y02E 50/10
See application file for complete search history.

(56) References Cited

U.S. PATENT DOCUMENTS

| | | | |
|---|---|---|---|
| 7,238,482 | B2 | 7/2007 | Picataggio et al. |
| 7,932,077 | B2 | 4/2011 | Damude et al. |
| 9,279,136 | B2 | 3/2016 | Franklin et al. |
| 2010/0234458 | A1 | 9/2010 | Dubreucq et al. |
| 2011/0252696 | A1 | 10/2011 | Franklin et al. |
| 2011/0263709 | A1 | 10/2011 | Hutchenson et al. |

FOREIGN PATENT DOCUMENTS

WO WO-2022178302 A1 8/2022

OTHER PUBLICATIONS

Botti A., PhD., Genetic and process engineering approaches for improving lipid productivity in the non-conventional oleaginous yeast Cutaneotrichosporon oleaginosus. Thesis, 2019, Univ., Bologna, Italy, pp. 1-81. (Year: 2019).*

Gao et al., Overproduction of fatty acid ethyl esters by the oleaginous yeast Yarrowia lipolytica through metabolic engineering and process optimization. ACS Synth. Biol., 2018, vol. 7: 1371-1380. (Year: 2018).*

Jamin et al., Determination of the 13C/12C Ratio of Ethanol Derived from Fruit Juices and Maple Syrup by Isotope Ratio Mass Spectrometry: Collaborative Study. J. AOAC Int., 2004, vol. 87(3): 621-631 (Year: 2004).*

Nakazawa et al., Temporal and spatial variations of carbon of atmospheric carbon dioxide in western Pacific region. J. Geophys. Res., 1997, vol. 102(D1): 1271-1285 (Year: 1997).*

Philippini et al., Agroindustrial byproducts for the generation of biobased products: alternatives for sustainable biorefineries. Front. Energy Res., 2020, vol. 8(152), pp. 1-23. (Year: 2020).*

Slininger et al., Comparative Lipid Production by Oleaginous Yeasts in Hydrolyzates of Lignocellulosic Biomass and Process Strategy for High Titers. Biotechnol. Bioeng., 2016, vol. 113(8): 1676-1690. (Year: 2016).*

Sitepu et al., C/N ratio Oleaginous yeasts for biodiesel: Current and future trends in biology and production. Biotechnol. Advan., 2014, JBA-06836, pp. 1-25 (Year: 2014).*

Wu et al., Ethanol and H2O2 stresses enhance lipid production in an oleaginous Rhodotorula toruloides thermotolerant mutant L1-1. FEMS Yeast Res., 2020, vol. 20(4), pp. 1-14. (Year: 2020).*

PCT/US2022/017064 International Search Report and Written Opinion dated Jun. 21, 2022.

Partial Supplementary European Search Report corresponding EP Application No. 227570306, dated Jul. 25, 2025, 16 pages.

Evans et al., "A comparison of the oleaginous yeast grown on different carbon sources in continuous and batch culture", LIPIDS, vol. 18, No. 9 (1983), 7 pages.

Minkevich et al., "The effect of lipid content on the elemental composition and energy capacity of yeast biomass", Appl. Microbiol. Biotechnol. (2010) 88:799-806.

Ganger et al., "Efficiency of Fatty Acid Synthesis by Oleaginous Yeasts: Prediction of Yield and Fatty Acid Cell Content from Consumed C/N Ratio by a Simple Method", Biotechnology and Bioengineering, vol. 42, pp. 1151-1 156 (1993).

Fei et al., "Exploring Low-cost Carbon Sources for Microbial Lipids Production by Fed-batch Cultivation of Cryptococcus albidus", Biotechnology and Bioprocess Engineering 16: 482-487 (2011).

Extended European Search Report corresponding EP Application No. 22757030.6, dated Oct. 16, 2025, 14 pages.

* cited by examiner

*Primary Examiner* — Ganapathirama Raghu
(74) *Attorney, Agent, or Firm* — Meunier Carlin & Curfman LLC

(57) ABSTRACT

SYSTEMS AND METHODS OF MAKING OIL FROM MICROORGANISMS Described herein are systems and methods of manufacturing an oil comprising a triacylglyceride. The systems and methods may comprise: (a) providing an oleaginous microorganism; (b) culturing the oleaginous microorganism in a medium comprising a carbon source, wherein the carbon source comprises ethanol at greater than 50% by weight; and (c) harvesting the oil from the oleaginous microorganism when the oil is at least 25% by weight of the oleaginous microorganism.

16 Claims, 9 Drawing Sheets

SYSTEMS AND METHODS OF MAKING OIL FROM MICROORGANISMS

CROSS-REFERENCE

This application is a continuation of International Patent Application PCT/US22/17064 filed on Feb. 18, 2022, which claims the benefit of U.S. Provisional Patent Application 63/150,937 filed on Feb. 18, 2021, each of which is incorporated herein by reference in its entirety.

BACKGROUND

Vegetable oil is one of the largest agricultural products in the world and is used extensively in most all processed and fried foods. The cultivation of these oils is a leading cause of deforestation and climate change.

SUMMARY

There is a significant need to provide alternative oils that are produced in a more sustainable manner. The search of feedstocks for production of these oils commonly leads to excessive land use and clearing of biologically diverse habitats. Alternative methods have been identified to produce oils by culturing microorganisms in the presence of a carbon source. However, these methods lend themselves to high costs and low oil yield. Thus, there is a need for new oil production processes that are more cost effective and provide high oil yields comprising TAGS. The present disclosure provides for systems and methods of making oils comprising TAGS using ethanol as a carbon source. The ethanol saves production costs by providing high oil yield and production rates. Using ethanol as a carbon source also allows for the co-location of an ethanol production facility with the oil production facility. This lowers the costs of oil production even further by decreasing costs of the production and transport of the ethanol.

The present disclosure provides a method of manufacturing an oil comprising a triacylglyceride. The method includes providing an oleaginous microorganism; culturing the oleaginous microorganism in a medium comprising a carbon source, wherein the carbon source comprises ethanol at greater than 50% by weight; and harvesting the oil from the oleaginous microorganism when the oil is at least 25% by weight of the oleaginous microorganism. In some cases, the oleaginous microorganism is yeast. In some cases, the yeast is *Cutaneosporon oleaginosus, Lipomyces tetrasporus, Rhodotorula toluroides*, or *Yarrowia Lypolytica*. In some cases, the carbon source can also include glucose. In some cases, the ethanol is present in the medium at a concentration of greater than 0.10%. In some cases, the oil has less than 7% omega-6 fatty acids by weight. In some cases, the oil has up to 7% omega-6 fatty acids by weight. In some cases, the oil has an oxidative stability index greater than 50 hours. In some cases, the ethanol is cellulosic ethanol. In some cases, the ethanol has a $^{13}C/^{12}C$ ratio similar to that of atmospheric carbon dioxide. In some cases, the oil has a $^{13}C/^{12}C$ ratio similar to that of atmospheric carbon dioxide. In some cases, the method includes sourcing ethanol from an ethanol manufacturing facility. In some cases, the method includes distilling the ethanol in a distillation column at the ethanol manufacturing facility and extracting the ethanol from a distillation column outlet. In some cases, the method includes co-manufacturing ethanol alongside the oil at an oil manufacturing facility. In some cases, culturing the oleaginous microorganism further comprises the use of an acid to maintain a desired pH. In some cases, culturing the oleaginous microorganism further comprises the use of a base to maintain a desired pH. In some cases, the method includes measuring a dissolved oxygen level during the process. In some cases, the method includes measuring a dissolved oxygen level in the medium. In some cases, culturing the oleaginous microorganism includes measuring a growth rate of the oleaginous microorganism. In some cases, culturing the oleaginous microorganism is performed at a temperature of greater than 24 degrees Celsius. In some cases, harvesting the oil includes performing an enzymatic hydrolysis on the oleaginous microorganism. In some cases, harvesting the oil includes centrifuging the oil from the medium.

In some cases, the oil has a lipid titer of at least about 10 g/L in the medium after culturing the oleaginous microorganism for 75 hrs. In some cases, the oil has a lipid titer of at least about 15 g/L in the medium before culturing the oleaginous microorganism for 150 hrs. In some cases, the oil has a lipid titer of at least about 20 g/L in the medium after culturing the oleaginous microorganism for 150 hrs. In some cases, the oil has a lipid titer of at least about 25 g/L in the medium before culturing the oleaginous microorganism for 200 hrs. In some cases, the oil has a lipid titer of at least about 28 g/L in the medium after culturing the oleaginous microorganism for 200 hrs. In some cases, the oil has a lipid titer of at least about 28 g/L in the medium before culturing the oleaginous microorganism for 250 hrs. In some cases, the oil has a lipid titer of at least about 28 g/L to 50 g/L of oleaginous microorganism at the time of the harvesting.

In some cases, the oil has a lipid percentage of at least about 30% of dry cell weight after culturing the oleaginous microorganism for 100 hrs.

In some cases, the oil has a lipid percentage of at least about 30% of dry cell weight after culturing the oleaginous microorganism for 150 hrs.

In some cases, the oil has a lipid percentage of at least about 50% of dry cell weight after culturing the oleaginous microorganism for 200 hrs.

In some cases, the oil has a lipid percentage of at least about 50% of dry cell weight after culturing the oleaginous microorganism for 250 hrs.

In some cases, the oil has a lipid titer of at least about 60% in the medium after culturing the oleaginous microorganism for 250 hrs.

In some cases, the ethanol is provided to the oleaginous microorganism at a rate of at least 1 g/L per hour.

In some cases, the ethanol is provided to the oleaginous microorganism at a rate of at least 1.4 g/L per hour.

In some cases, the oleaginous microorganism has a biomass concentration of at least 25 g/L after culturing the oleaginous microorganism for at least 50 hrs.

In some cases, the oleaginous microorganism has a biomass concentration of at least 25 g/L before culturing the oleaginous microorganism for 100 hrs.

In some cases, the oleaginous microorganism has a biomass concentration of at least 35 g/L after culturing the oleaginous microorganism for at least 75 hrs.

In some cases, the oleaginous microorganism has a biomass concentration of at least 35 g/L before culturing the oleaginous microorganism for 150 hrs.

In some cases, the oleaginous microorganism has a biomass concentration of at least 50 g/L after culturing the oleaginous microorganism for 150 hrs.

In some cases, the oleaginous microorganism has a biomass concentration of at least 50 g/L before culturing the oleaginous microorganism for 200 hrs. In some cases, the oil is at least about 25% C16:0 fatty acid. In some cases, the oil is at least about 30% C16:0 fatty acid. In some cases, the oil is at least about 15% C18:0 fatty acid. In some cases, the oil is at least about 20% C18:0 fatty acid. In some cases, the oil is at least about 35% C18:1 fatty acid.

In some cases, the oil is at least about 40% C18:1 fatty acid. In some cases, the oil is at least about 2% C18:2 fatty acid. In some cases, the oil is at least about 5% C18:2 fatty acid. In some cases, the oil is at least about 5% C16:1 fatty acid.

In another aspect, the present disclosure provides a manufacturing system including an ethanol production unit having a first outlet comprising an ethanol product with an increased purity and a second outlet comprising an ethanol product with a reduced purity; and an oil production unit having an inlet for receiving the ethanol product with a reduced purity from the second outlet and a bioreactor comprising an oleaginous microorganism producing oil from the ethanol product with a reduced purity. In some cases, the ethanol product with an increased purity has a purity of greater than 50%. In some cases, the first outlet is directed to a first refining unit that generates an alcoholic product comprising industrial ethanol, beer, or vodka. In some cases, the oil production unit includes a second inlet for receiving an additional carbon source. In some cases, the additional carbon source is glucose. In some cases, the second outlet includes cellulosic ethanol. In some cases, the bioreactor includes cellulosic sugars. In some cases, the ethanol product with a reduced purity has a purity of less than 50%. In some cases, the oil produced by the oleaginous microorganism includes less than 7% omega-6 fatty acids by weight. In some cases, the oil produced by the oleaginous microorganism includes up to 7% omega-6 fatty acids by weight. In some cases, the oil produced by the oleaginous microorganism has an oxidative stability index greater than 50 hours. In some cases, the oil production unit includes a pH monitor configured to measure a pH in the bioreactor. In some cases, the bioreactor includes a base configured to maintain a desired pH. In some cases, the bioreactor includes an acid configured to maintain a desired pH. In some cases, the oil production unit includes a dissolved oxygen monitoring unit for measuring an oxygen level in the bioreactor while the oleaginous microorganism produces oil from the ethanol product with a reduced purity. In some cases, the dissolved oxygen level is greater than 10%. In some cases, the oil production unit includes a growth rate monitoring unit for measuring a growth rate of the oleaginous microorganism. In some cases, the growth rate is greater than 0.05 $h^{-1}$. In some cases, the oil production unit includes an oil monitoring unit for measuring an oil titer in the bioreactor while the oleaginous microorganism produces oil from the ethanol product with a reduced purity. In some cases, the oil titer is greater than 50 grams of oil per liter of medium. In some cases, the oil production unit includes an enzymatic hydrolysis reactor. In some cases, the oil produced by the oleaginous microorganism is harvested by performing an enzymatic hydrolysis on the oleaginous microorganism in the enzymatic hydrolysis reactor. In some cases, the oil production unit includes a centrifuge. In some cases, the oil produced by the oleaginous microorganism is harvested by centrifuging the oil from the medium.

In another aspect, the present disclosure provides a method of manufacturing an oil comprising a triacylglyceride, the method comprising: a) culturing an oleaginous microorganism in a medium comprising a carbon source, wherein the carbon source does not comprise ethanol or comprises ethanol at a concentration no greater than 50% by weight; b) adding ethanol to the medium so that the carbon source comprises ethanol at a concentration greater than 50% by weight and further culturing the oleaginous microorganism in the medium; c) harvesting the oil from the oleaginous microorganism when the oil is at least 50% of the dry cell weight of the oleaginous microorganism.

In some cases, the ethanol is added to the medium in step b) at a rate of 0.5 to 1.5 g/L/h.

In some cases, the ethanol is added intermittently. In some cases, the ethanol is added at a variable rate. In some cases, the ethanol is added at a rate that maintains the concentration of ethanol in the medium at a concentration of 20 to 25 g/L during step b). In some cases, the adding of ethanol in step b) is started 12-48 hours after the beginning of step a).

In some cases, the adding of ethanol in step b) is started after the culturing of step a) results in the biomass of the oleaginous microorganism reaching 10 to 30 g/L in the medium by dry cell weight. In some cases, the carbon source in step a) comprises a sugar. In some cases, the concentration of the sugar at the beginning of step a is from 20 to 40 g/L in the medium.

In some cases, the sugar concentration in the medium is reduced due to consumption of the sugar by the oleaginous microorganism. In some cases, the adding of ethanol in step b) is started after the sugar is reduced to less than 10 g/L in the medium. In some cases, the additional sugar is not added after the beginning of step a). In some cases, the sugar is glucose. In some cases, at the time of the harvesting of step c), the oleaginous microorganism is present in the medium at a concentration of least 40 g/L by dry cell weight.

In some cases, at the time of the harvesting of step c), the lipid titer in the medium is at least 20 g/L.

In some cases, the harvesting yields at least about 0.2 grams of oil per gram of ethanol added in step b).

In some cases, steps a) and b) are performed in a bioreactor in a fed-batch process.

In some cases, steps a) and b) are performed in a bioreactor in a continuous culture process.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "FIG." herein), of which:

DETAILED DESCRIPTION

Figure 1:
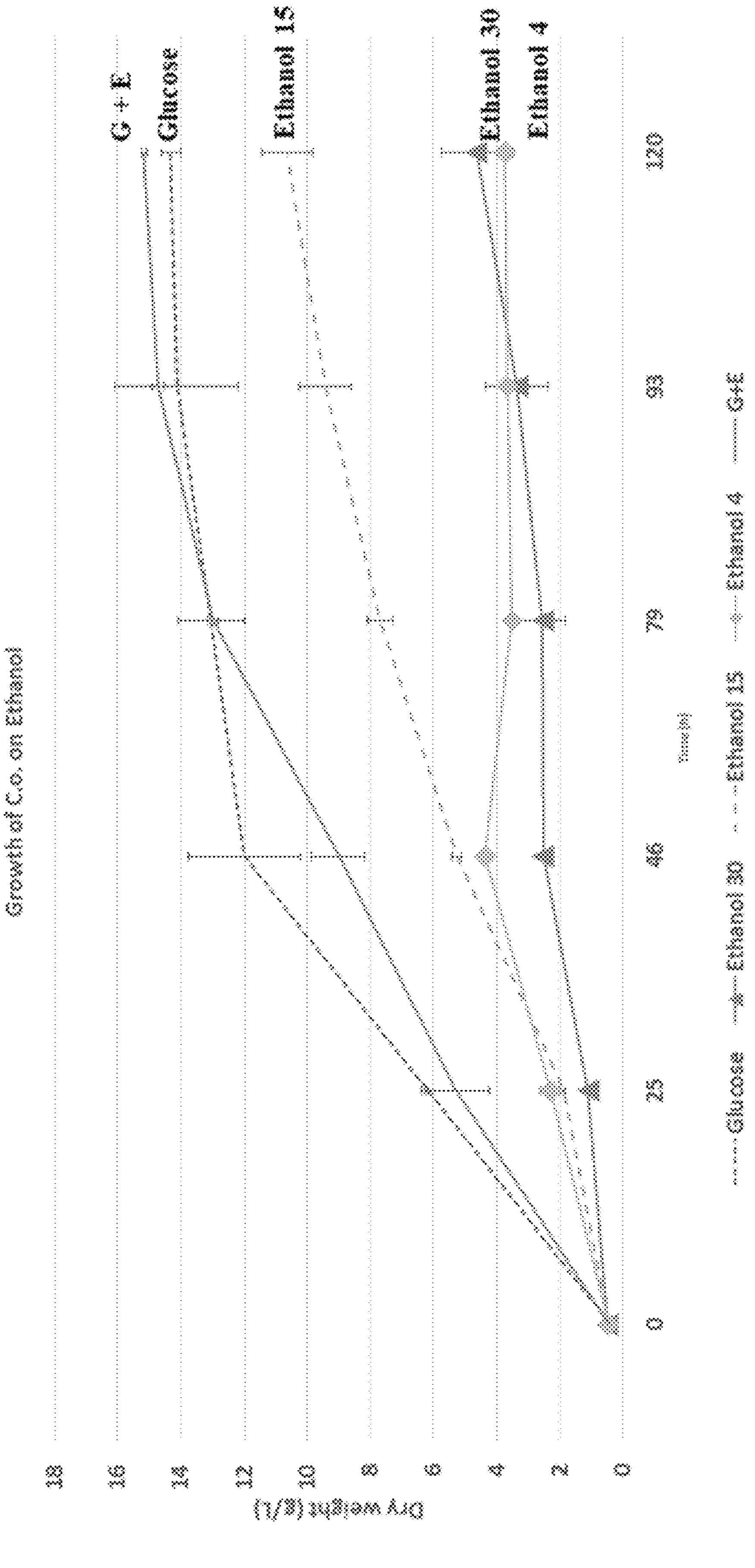
FIG. 1 illustrates growth of *Cutaneotrichosporon oleaginosus* in ethanol.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "about" when referring to a number or a numerical range generally means that the number or numerical range referred to is an approximation within experimental variability (or within statistical experimental error), and thus the number or numerical range may vary from, for example, between 1% and 15% of the stated number or numerical range.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

Overview

The search of feedstocks for production of oils commonly leads to excessive land use and clearing of biologically diverse habitats. Alternative methods have been identified to produce oils by culturing microorganisms in the presence of a carbon source. However, these methods lend themselves to high costs and low oil yield. Thus, there is a need for new oil production processes that are more cost effective and provide high oil yields comprising TAGS. The present disclosure provides for systems and methods of making oils comprising TAGS using ethanol as a carbon source. The ethanol saves production costs by providing high oil yield and production rates. Using ethanol as a carbon source also allows for the co-location of an ethanol production facility with the oil production facility. This lowers the costs of oil production even further by decreasing costs of the production and transport of the ethanol.

I. Methods of Manufacturing Oils Using Ethanol as a Carbon Source

In an aspect, the present disclosure provides for a method of manufacturing an oil comprising a triacylglyceride (TAG). The method may comprise: (a) providing an oleaginous microorganism; (b) culturing the oleaginous microorganism in a medium comprising a carbon source, wherein the carbon source comprises ethanol at greater than 50% by weight; and (c) harvesting the oil from the oleaginous microorganism when the oil is at least 50% by weight of the oleaginous microorganism.

The method may include, before step (b), adding ethanol to the medium, thereby causing the carbon source to comprise ethanol at greater than 50% by weight.

In another aspect, the present disclosure provides a method of manufacturing an oil. The oil may include a triacylglyceride. The method may include culturing an oleaginous microorganism in a medium comprising a carbon source. The carbon source may not comprise ethanol. The carbon source may not comprise ethanol at a concentration no greater than 50% by weight. The method may also include adding ethanol to the medium so that the carbon source comprises ethanol at a concentration greater than 50% by weight and further culturing the oleaginous microorganism in the medium. The method may include harvesting the oil from the oleaginous microorganism when the oil is at least 50% of the dry cell weight of the oleaginous microorganism. In some cases, culturing an oleaginous microorganism in a medium comprising a carbon source, wherein the carbon source does not comprise ethanol or comprises ethanol at a concentration no greater than 50% by weight. In some cases, the ethanol may not be at a concentration greater than 40%, 30%, 20%, 10%, or 5%, of said carbon source. In some cases, the carbon source does not comprise ethanol in step a).

II. Co-location of an Ethanol Production Unit and an Oil Production Unit

In additional embodiments according to the present disclosure, a system is provided for the co-manufacturing of ethanol and oil at the same site. The systems may comprise an ethanol production unit comprising a first outlet comprising an ethanol product with an increased purity and a second outlet comprising an ethanol product with a reduced purity relative to the first outlet. The system may further comprise an oil production unit comprising one or more inlets and a bioreactor. An inlet of the oil production unit may be configured to receive the ethanol product with a reduced purity from the second outlet of the ethanol production unit. The bioreactor of the oil production unit may be configured to hold a growth medium comprising an oleaginous microorganism that can produce oil from the ethanol with a reduced purity.

III. Oleaginous Microorganisms

In the systems and methods described herein, the oil is generated by a microorganism. The microorganism may be for example, yeast. The yeast can be used to synthesize TAGS. The utilization of yeast for oil may be advantageous over other sources such as microalgae or vegetable oils. Cultivation of yeasts in comparison to cultivation of plants to produce vegetable oil may be less affected by environmental conditions, seasonal production, or geographic locations. Additionally, yeasts may grow faster than microalgae, and be more resistant against climatic and seasonal changes. In some cases, the trace compounds of oil from yeast may be different than the trace compounds generated from microalgae and higher plants leading to an oil fingerprint. In some cases, the oil may be generated from a non-photosynthetic microorganism. The non-photosynthetic microorganism may generate an oil (e.g., a non-photosynthetic microbial oil).

The oil may be generated from yeast that may come from the genera *Agaricomycotina, Ascomycota, Basidiomycota, Candida, Chlorellales, Chlorellaceae, Cryptococcus, Cuniculitremaceae, Debaryomycetaceae, Filobasidiales, Incertae sedis, Lipomyces, Metschnikowiaceae, Pichiaceae, Rhodosporidium, Rhodotorula, Rhizpus, Saccharaomycotina, Saccharomycetes, Saccharomycetales, Tremellomycetes, Trichomonoascaceae, Trichosporon, Trichosporonales, Viridiplantae*, or *Yarrowia*, etc. The yeast may be, for example, *Cutaneotrichosporon oleaginous, Rhodotorula toluroides, Rhodosporidium toruloides, Lipomyces starkeyi, Lipomyces lipofer, Lipomyces arxii, Lipomyces doorenjongii, Lipomyces oligophage, Lipomyces spencer-martinsiae, Lipomyces knonenkoae, Lypomyces tetrasporus, Lipomyces anomalus, Lipomyces japonicus, Lipomyces kockii, Lipomyces kononenkoae, Lipomyces mesembrius, Rhodosporidium* sp., *Rhodotorula* sp., *Yarrowia* sp., *Yarrowia lipolytica, Cryptococcus* sp., *Cryptococcus aerius, Lipomyces* sp., *Candida curvata, Candida aff. insectorum, Candia aff sagamina, Candida aff. kazuoi, Rhodotorula glutinis, Rhodotorula graminis, Rhodotula* 110, *Rhodotorula aurantiaca, Leucosporidiella creatinivora, Rhodotorula colostri, Rhodotorula dairenensis, Rhodotorula mucilaginosa, Rhodosporidium babjevae, Rhodosporidium diobovatum, Rhodosporidium fluviale, Rhodosporidium paludigenum, Rhodosporidium sphaerocarpum, Rhodosporidium toruloides, Cryptococcus podzolicus, Trichosporon porosum, Trichosporon guehoae, Pichia segobiensis, Trichosporonoides spathulata, Kodamaea ohmeri, Cryptococcus* sp., *Cryptococcus music, Lipomyces tetrasporus, Lipomyces* sp, *Myxozyma geophila, Myxozyma lipomycoides, Myxozyma mucilagina, Myxozyma udenii, Myxozyma vanderwaltii, Myxozyma cf. melibiosi, Myxozyma melibiosis, Torulaspora delbrueckii, Trigonopsis varaibilis, Cutaneotrichosporon oleaginosus, Cutaneosporon oleaginosus, Scheffersomyces stipitis, Kurtzmaniella cleridarum, Pichia manshurica, Cuniculitrema polymorpha, Filobasidium loriforme, Filobasidium globisporum, Filobasidium aff. globisporum, Filobasidium inconspicuum, Cryptococcus albidus, Cryptococcus gastricus, Cryptococcus magnus, Cryptococcus oeirensis, Cryptococcus terreus, Cryptococcus aff. taibaiensis, Cryptococcus lavescens, Cryptococcus aff. laurentii, Cryptococcus luteolus, Cryptococcus victoriae, Cryptococcus cf. curvatus, Cryptococcus humicola, Cryptococcus ramirezgomezianus, Cryptococcus wieringae, Filobasidium cf. uniguttulatus, Hannaella aff zeae, Tremella aurantia, Tremella enchepala, Prototheca aff. zopii, Prototheca stagnora, Prototheca aff. zopii* var. *hydrocarbonea, Prototheca zopii* var. *zopii*, ATCC 20509, or *Metschnikowia pulcherrim*, etc. In some cases, the yeast may be a recombinant yeast. In other cases, the yeast may be a chemically or physically induced mutant of a natural or recombinant yeast. The oil may be extracted from the yeast upon production.

IV. Ethanol and Other Carbon Sources

Yeast may accumulate lipids intracellularly when the carbon source is present in excess. In some cases, nitrogen limitation may be used to induce lipogenesis. In other cases, other nutrient limitation, such as phosphorus, magnesium, sulfur, or iron limitation may be used to induce lipogenesis. In some cases, lipogenesis occurs in the absence of a limited nutrient. The yeast may use one or more different carbon sources for the production of cell mass and/or lipids. These sources can be, for example, starch, ethanol, industrial ethanol, acetic acid, glucose, fructose, sucrose, raffinose, molasses, bagasse, xylose, glycerol, methanol, synthesis gas, carbon dioxide, carbon monoxide, formic acid, cellulose hydrolysates, and industrial, agricultural, food, and municipal organic wastes.

In the systems and methods described herein, the source comprises ethanol. In other cases, the source comprises acetic acid. In some cases, the source may be a blend of carbon sources. In some cases, the source of the carbon source is from a fossil source and/or a renewable bio-based source. The major lipid components of oleaginous yeasts may be triacylglycerols. The triacylglycerols may be composed of, for example, C16 to C18 series long chain fatty acids. The triacylglycerols may be also composed of, for example, C1 to C6 series short chain fatty acids. The triacylglycerols may be as described elsewhere herein.

In some embodiments, the carbon source comprises solely ethanol. In other embodiments, the carbon source comprises ethanol and glucose. In some embodiments, the carbon source may also include, for example, starch, ethanol, industrial ethanol, acetic acid, glucose, fructose, sucrose, raffinose, molasses, bagasse, xylose, glycerol, methanol, synthesis gas, carbon dioxide, carbon monoxide, formic acid, cellulose hydrolysates, and industrial, agricultural, food, and municipal organic wastes. In some embodiments, the ethanol may be present in the carbon source at greater than 10% by weight, greater than 20% by weight, greater than 30% by weight, greater than 40% by weight, greater than 50% by weight, greater than 60% by weight, greater than 70% by weight, greater than 80% by weight, or greater than 90% by weight of the total carbon source. The ethanol may be present in the carbon source at a weight percentage in a range of about 20% to about 40%, 20%, to about 50%, 50% to about 70%, or 50% to about 90% of the total carbon source.

In some embodiments, the carbon source may initially be one carbon source but may then be switched to another carbon source. In some cases, the initial carbon source may be glucose while the second carbon source may be ethanol. In some cases, the cells may be propagated in media with at least 50% of carbon source being ethanol. In some cases, the cells may be propagated in media with at least about 20%, 30%, 40%, 50%, 60%, 70%, or more, of carbon source being ethanol. In some cases, the growth in the tanks may begin with glucose and then transitioned to ethanol to support lipid production.

The ethanol, or carbon sources used, may provide a high yield of oil in the oleaginous microorganism. The yield of oil may be defined as the weight percentage of the oil in the microorganism at the completion of the culturing process. For example, the oleaginous microorganism may comprise the oil at greater than about a 20%, 30%, 40%, 50%, 60%, 70%, 80%, or 90% or higher weight percentage at the completion of the culturing process. The microorganism may comprise the oil in a range of about a 20% to about 40%, 20% to about 50%, 50% to about 70%, or 50% to about 90% weight percentage.

The ethanol may be present in the medium at a concentration of greater than 0.1%, 0.2%, 0.3%, 0.4%, 0.5%, 0.6%, 0.7%, 0.8%, 0.9%, 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10.0% or 15.0%.

The ethanol in the carbon source may comprise cellulosic ethanol. The ethanol may comprise an isotope fractionation, or $^{13}C/^{12}C$ ratio, similar to that of atmospheric carbon dioxide or plants. Similar to means that the ethanol may have a $^{13}C/^{12}C$ ratio in the same range of atmospheric carbon dioxide or plants as compared to the $^{13}C/^{12}C$ ratio of fossil feedstocks, such as petroleum or coal. Isotope fractionation occurs during physical processes and chemical reactions, and is accounted for during radiocarbon measurements. Isotope fractionation results in enrichment of one isotope over another isotope. In the carbon cycle of plants, isotope fractionation occurs. During photosynthesis, the relative amounts of different carbon isotopes that are consumed are 12C>13C>14C, due to slower processing of heavier isotopes. Plants species exhibit different isotope fractionation due to isotopic discrimination of photosynthetic enzymes and diffusion effects of their stomata. For example, C3 plants exhibit different isotope fractionation than C4 plants. The $^{13}C/^{12}C$ ratio of renewable carbon sources is usually indicated as a negative number and indicates how close the carbon content is to a control, which may be a substance comprising carbon derived from fossil fuels (e.g., petroleum). A higher negative number indicates a renewable carbon source.

The $^{13}C/^{12}C$ ratio of the ethanol may be between about −32 to about −6 0/100. The $^{13}C/^{12}C$ ratio may be between about −10 to about 0 0/100. The $^{13}C/^{12}C$ ratio may be between about −20 to about −10 0/100. The $^{13}C/^{12}C$ ratio may be between about −30 to about −20 0/100. The $^{13}C/^{12}C$ ratio may be between about −40 to about −30 0/100. The $^{13}C/^{12}C$ ratio may be between about −50 to about −40 0/100. The $^{13}C/^{12}C$ ratio may be between about −60 to about −50 0/100. The $^{13}C/^{12}C$ ratio may be between about −70 to about −60 0/100. The $^{13}C/^{12}C$ ratio may be between about −80 to about −70 0/100. The $^{13}C/^{12}C$ ratio may be between about −90 to about −80 0/100. And the $^{13}C/^{12}C$ ratio may be between about −100 to about −90 0/100. The $^{13}C/^{12}C$ ratio may be less than 0 0/100, −10 0/100, −20 0/100, −30 0/100, −40 0/100, −50 0/100, −60 0/100, −70 0/100, −80 0/100, or −90 0/100 or lower.

The method of manufacturing the oil comprising a TAG may also comprise sourcing the ethanol used in the growth medium from an ethanol manufacturing facility. The ethanol from the ethanol manufacturing facility may come from a product stream of one or more distillation columns in the ethanol manufacturing facility. For example, the ethanol may be derived from a product stream of a first distillation tower of an ethanol plant and the ethanol can be in the product stream at a concentration of less than about 50%. The ethanol may also be in a product stream of a first distillation towel at a concentration of less than about 10%, 20%, 30%, or 40%. The ethanol may also be in a product stream of a fermentation tank at a concentration of less than about 10%, 20%, 30%, or 40%. The ethanol may also be derived from a product stream from a second distillation tower of an ethanol distillation tower. For example, the ethanol may be derived from a product stream of a second distillation tower of an ethanol plant and the ethanol can be in the product stream at a concentration of greater than about 50%. The ethanol may also be in a product stream of a second distillation tower at a concentration of greater than about 60%, 70%, 80%, or 90% or greater. Additionally, the ethanol may be derived from a product stream of a third distillation tower of an ethanol manufacturing plant. For example, the ethanol may be derived from a product stream of a third distillation tower of an ethanol plant and the ethanol can be in the product stream at a concentration of greater than about 95%. In certain embodiments, the ethanol manufacturing facility and an oil manufacturing facility can be two separate facilities. In additional embodiments, the ethanol can be co-manufactured alongside the oil at an oil manufacturing facility.

In some embodiments, the ethanol may be provided to the oleaginous microorganism at a given rate. In some cases, the ethanol may be added intermittently. In some cases, the ethanol may be added at a variable rate. In some cases, the ethanol may be provided to the oleaginous microorganism at a rate of a least about 0.5 gram per liter (g/L) per hour, 0.75 g/L per hour, 1 g/L per hour, 1.25 g/L per hour, 1.3 g/L per hour, 1.4 g/L per hour, 1.5 g/L per hour, 1.6 g/L per hour, 1.75 g/L per hour, 1.80 g/L per hour, 1.90 g/L per hour, 2.0 g/l per hour, or more. In some cases, the ethanol may be provided to the oleaginous microorganism at a rate of a most about 2.0 g/l per hour, 1.90 g/L per hour, 1.80 g/L per hour, 1.75 g/L per hour, 1.6 g/L per hour, 1.5 g/L per hour, 1.4 g/L per hour, 1.3 g/L per hour, 1.25 g/L per hour, 1 g/L per hour, 0.75 g/L per hour, 0.5 gram per liter (g/L) per hour, or less. In some cases, the ethanol may be provided to the oleaginous microorganism at a rate from 0.5 g/L per hour to 2.0 g/L per hour, 1.0 g/L per hour to 2.0 g/L per hour, 1.5 g/L per hour to 2.0 g/L per hour, 0.5 g/L per hour to 1.5 g/L per hour, or 1.0 g/L per hour to 1.5 g/L per hour. In some embodiments, the ethanol may be provided to the oleaginous microorganism at a rate of at least 1 g/L per hour. In some cases, the ethanol may be provided to the oleaginous microorganism at a rate of at least 1.4 g/L per hour.

In some cases, the ethanol may be added at a rate that maintains the concentration of ethanol in the medium during the addition of ethanol to the medium. In some cases, the ethanol may be added at a rate that maintains the concentration of ethanol in the medium at a concentration of 20 to 25 g/L during adding ethanol to the medium.

In some cases, the ethanol may be added at a rate that maintains the concentration of ethanol in the medium at a concentration of at least about 10 g/L, 15 g/L, 20 g/L, 25 g/L, 30 g/L, 35 g/L, 40 g/L, or more during adding ethanol to the medium. In some cases, the ethanol may be added at a rate that maintains the concentration of ethanol in the medium at a concentration of at most about 40 g/L, 35 g/L, 30 g/L, 25 g/L, 15 g/L, 10 g/L, or more during adding ethanol to the medium. In some cases, the ethanol may be added at a rate that maintains the concentration of ethanol in the medium at a concentration from about 10 g/L to 40 g/L, 15 g/L to 35 g/L, 20 g/L to 30 g/L or 20 to 25 g/L.

In some cases, adding of ethanol to the medium may be started 12-48 hours after the initial culturing of the oleaginous microorganism. In some cases, the ethanol may be added to the medium at least 6 hrs, 12 hrs, 18 hrs, 24 hrs, 30 hrs, 36 hrs, 42 hrs, 48 hrs, 72 hrs, or more after the initial culturing of the oleaginous microorganism. In some cases, the ethanol may be added to the medium at most 72 hrs, 48 hrs, 42 hrs, 36 hrs, 30 hrs, 24 hrs, 18 hrs, 12 hrs, 6 hrs, or less after the initial culturing of the oleaginous microorganism. In some cases, adding of ethanol to the medium may be started between 6 hrs to 72 hrs, 6 hrs to 48 hrs, 6 hrs to 24 hrs, 6 hrs to 12 hrs, 12 hrs to 48 hrs, 24 hrs to 48 hrs, or 36 hrs to 48 hrs after the initial culturing of the oleaginous microorganism.

In some embodiments, the adding of ethanol in step b) may be started after the culturing of step a) results in the biomass of the oleaginous microorganism reaching 10 to 30 g/L in the medium by dry cell weight. In some embodiments, the adding of ethanol may be started after the culturing of the oleaginous microorganism results in the biomass of the oleaginous microorganism reaching at least about 1 g/L, 5 g/L, 10 g/L, 15 g/L, 20 g/L, 25 g/L, 30 g/L, 35 g/L, 40 g/L, 45 g/L, 50 g/L or more in the medium by dry cell weight. In some embodiments, the adding of ethanol may be started after the culturing of the oleaginous microorganism results in the biomass of the oleaginous microorganism reaching about 1 g/L to 50 g/L, 10 g/L to 50 g/L, 15 g/L to 40 g/L, 20 g/L to 35 g/L, 25 g/L to 30 g/L, 5 g/L to 25 g/L, or 5 g/L to 20 g/L, in the medium by dry cell weight.

In some embodiments, the carbon source may include one or more sugars. The sugar may be a 5-carbon sugar. The sugar may be a 6-carbon sugar. The sugar may be a monosaccharide. The sugar may be a disaccharides. The sugar may be a mixture of different sugars. The sugar may be selected from, for example, glucose, fructose, galactose, sucrose, lactose, maltose, dextrose, maltodextrin, etc. The carbon source may include one or more non-sugar carbon sources. The non-sugar carbon sources may be selected from starch, glycerol, cellulosic biomass, methane, methanol, syn gas, or other suitable carbon sources known in the art, etc, In some cases, the concentration of the sugar at the beginning of culturing the oleaginous microorganism may be at least about 10 g/L, 15 g/L, 20 g/L, 25 g/L, 30 g/L, 35 g/L, 40 g/L, 50 g/L, or more. The concentration of the sugar at the beginning of culturing the oleaginous microorganism may be at most about 50 g/L, 40 g/L, 35 g/L, 30 g/L, 25 g/L, 15 g/L, 10 g/L, or less. In some cases, the concentration of the sugar at the beginning of culturing the oleaginous microorganism may be from about 10 g/L to 40 g/L, 20 g/L to 40 g/L, 15 g/L to 35 g/L, 20 g/L to 30 g/L or 20 to 25 g/L.

In some embodiments, the sugar concentration in the medium may be reduced due to consumption of the sugar by the oleaginous microorganism. In some cases, adding of ethanol (e.g., in step b) may be started after the sugar is reduced to less than about 2 g/L, 3 g/L, 4 g/L, 5 g/L, 6 g/L, 7 g/L, 8 g/L, 9 g/L, 10 g/L, 12 g/L, 15 g/L, or 20 g/L.

In some embodiments, additional sugar may not be added after the beginning of step a).

In some embodiments, the oil may have a particular percentage of a particular fatty acid. The oil may have a C16:0 fatty acid percentage of at least about 20%, 25%, 27%, 30%, 32%, 35%, 40%, 50%, or more. The oil may have a C16:0 fatty acid percentage of at most about 50%, 40%, 35%, 32%, 30%, 27%, 25%, 20%, or less. The oil may have a C16:0 fatty acid percentage from about 20% to 50%, 20% to 40%, 20% to 30%, 25% to 40%, 30% to 40%, 35% to 40%, or 28% to 35%.

The oil may have a C16:1 fatty acid percentage of at least about 0%, 1%, 2%, 3%, 4%, 5%, 6%, 7%, 8%, 9%, 10%, or more. The oil may have a C16:1 fatty acid percentage of at most about 10%, 9%, 8%, 7%, 6%, 5%, 4%, 3%, 2%, 1%, or less. The oil may have a negligible percentage of a C16:1 fatty acid. The oil may have a C16:1 fatty acid percentage from about 0% to 10%, 0% to 9%, 0% to 8%, 0% to 7%, 0% to 6%, or 0% to 5%.

In some embodiments, the oil may have a C18:0 fatty acid percentage of at least about 5%, 6%, 7%, 8%, 9%, 10%, 11%, 12%, 13%, 14%, 1, 1$^{6}$%, 1$^{7}$%, 18%, 19%, 20%, 25%, 30%, or more. The oil may have a C18:0 fatty acid percentage of at most about 30%, 25%, 20%, 19%, 18%, 17%, 16%, 15%, 14%, 13%, 12%, 11%, 10%, 9%, or less. The oil may have a negligible percentage of a C18:0 fatty acid. The oil may have a C18:0 fatty acid percentage from about 7% to 25%, 8% to 22%, 9% to 21%, or 8% to 12%. In some cases, the oil may have at least about 15% C18:0 fatty acid.

In some embodiments, the oil may have a C18:1 fatty acid percentage of at least about 35%, 40%, 42%, 45%, 50%, or more. The oil may have a C18:1 fatty acid percentage of at most about 50%, 45%, 42%, 40%, 35% or less. The oil may have a C18:1 fatty acid percentage from about 35% to 50%, 40% to 45%, 40% to 50%, 37% to 45%, 40% to 48%, or 45% to 50%. In some cases, the oil may be at least about 35% C18:1 fatty acid. In some cases, the oil may be at least about 40% C18:1 fatty acid.

The oil may have a C18:2 fatty acid percentage of at least about 0%, 1%, 2%, 3%, 4%, 5%, 6%, 7%, 8%, 9%, 10%, or more. The oil may have a C18:2 fatty acid percentage of at most about 10%, 9%, 8%, 7%, 6%, 5%, 4%, 3%, 2%, 1%, or less. The oil may have a C18:2 fatty acid percentage from about 0% to 10%, 0% to 9%, 0% to 8%, 0% to 7%, 0% to 6%, or 0% to 5%. In some cases, the oil may be at least about 2% C18:2 fatty acid. In some cases, the oil may be at least about 5% C18:2 fatty acid.

The oil may have a C18:3 fatty acid percentage of at least about 0%, 1%, 2%, 3%, 4%, 5%, 6%, 7%, 8%, 9%, 10%, or more. The oil may have a C18:3 fatty acid percentage of at most about 10%, 9%, 8%, 7%, 6%, 5%, 4%, 3%, 2%, 1%, or less. The oil may have a negligible percentage of a C18:3 fatty acid. The oil may have a C18:3 fatty acid percentage from about 0% to 10%, 0% to 9%, 0% to 8%, 0% to 7%, 0% to 6%, or 0% to 5%.Additional sources of ethanol for use in the growth medium can be industrial ethanol, crude unrefined ethanol, ethanol derived from petroleum, ethanol derived from sugar cane, ethanol derived from corn, ethanol derived from sugar beet, ethanol derived from wheat, ethanol derived from rice, ethanol derived from starch, ethanol derived from cellulosic biomass, ethanol derived from industrial waste, ethanol derived from steel mill flu gas, and ethanol derived from synthesis gas. The ethanol may also be commercial fuel grade ethanol or commercial food/spirit grade ethanol. The carbon source may also comprise other alcoholic substances such as beer and vodka.

In embodiments for the co-location of an ethanol production unit and an oil production unit, the ethanol may be as described herein. The ethanol production unit may produce ethanol via distillation, refining, fermentation, or other related methods. In additional embodiments, the second outlet of the ethanol production unit may comprise ethanol in a concentration of less than about 50%. The ethanol in the second outlet may also be in a concentration of less than about 10%, 20%, 30%, or 40%. The ethanol in the first outlet of the ethanol production unit may be in a concentration of greater than 50%. The ethanol in the first outlet may also be in a concentration of greater than 60%, 70%, 80%, or 90%. The first outlet may be directed to a first refining unit that generates an alcoholic product comprising beer or vodka. The ethanol in the first or second outlet of the ethanol production unit may be cellulosic ethanol.

The second outlet of the ethanol production unit may comprise ethanol at a volume percentage of less than about 50%. The ethanol in the second outlet may also be in a volume percentage of less than about 10%, 20%, 30%, or 40%. The ethanol in the first outlet of the ethanol production unit may comprise ethanol at a volume percentage of greater than 50%. The first outlet of the ethanol production unit may also comprise ethanol at a volume percentage of greater than 60%, 70%, 80%, or 90%.

The oil production unit may further comprise a second inlet configured to receive an additional carbon source. The additional carbon source may be glucose or other cellulosic sugars. The additional carbon sources can also be, for example, starch, acetic acid, fructose, sucrose, raffinose, molasses, bagasse, xylose, glycerol, methanol, synthesis gas, carbon dioxide, carbon monoxide, formic acid, cellulose hydrolysates, and industrial, agricultural, food, and municipal organic wastes. In certain embodiments, the ethanol and additional carbon sources may mix before entering the bioreactor.

V. Manufacturing Parameters Considered

In certain embodiments, the systems and methods comprise culturing the oleaginous microorganism in the medium comprising the carbon source. There are several factors that may be taken into account while the oleaginous microorganism is culturing in the medium. During the process, the pH of the medium can be constantly measured using a pH reader to ensure a desired pH is maintained throughout the process. For example, the oil production unit may comprise a pH monitor configured to measure the pH of the medium inside the bioreactor. If it is determined that the pH of the medium is reaching a level that is too high relative to a desired pH, then an acid may be added into the medium to help maintain the pH. Examples of acids that can be used to maintain the pH are acetic acid, phosphoric acid, hydrochloric acid, sulfuric acid, etc. If it is determined that the pH of the medium is reaching a level that is too low relative to a desired pH, then a base may be added into the medium to help maintain the pH. Examples of bases that can be used to help maintain the pH are, sodium hydroxide, ammonium hydroxide, potassium hydroxide, ammonia, etc.

A desired pH of the medium allowing growth of the oleaginous microorganism can be in a range of about 5.5 to about 6.5. A desired pH of the medium may also be about 4.0 to about 4.5, about 4.5 to about 5.0, about 5.0 to about 5.5, about 5.5 to about 6.0, about 6.0 to about 6.5, about 6.5 to about 7.0, about 7.0 to about 7.5, about 7.5 to about 8.0, about 8.0 to about 8.5, about 8.5 to about 9.0, about 9.0 to about 9.5, or about 9.5 to about 10.0. A desired pH may be up to about 5.0, 5.5, 6.0, 6.5, 7.0, 7.5, 8.0, 8.5, 9.0, 9.5, or 10.0. A desired pH may be less than 10.0, 9.5, 9.0, 8.5, 8.0, 7.5, 7.0, 6.5, 6.0, 5.5, or 5.0.

In certain embodiments the systems and methods may also comprise measuring an oxygen consumption rate in the cells of the oleaginous microorganism. For example, the oil production unit may comprise an oxygen consumption monitoring unit to measure an oxygen consumption rate inside the bioreactor. The oxygen consumption rate can be measured with the use of a polarographic oxygen electrode configured to measure the extracellular oxygen concentration inside the bioreactor. The oxygen consumption rate can also be measured through the use of optical techniques, wherein oxygen-dependent quenching of fluorophores determines oxygen concentration in the medium at a surface above the oleaginous microorganisms.

Additionally, a dissolved oxygen level in the medium can also be measured throughout the manufacturing process in the systems and methods described herein. For example, the oil production unit may comprise a dissolved oxygen monitoring unit configured to measure the dissolved oxygen of the medium inside the bioreactor. As an example, the dissolved oxygen in the medium can be measured using wet chemical techniques, where a medium sample can be collected and then subject to a chemical reaction used to determine the dissolved oxygen level. Additionally, membrane dissolved oxygen sensors can be used, where a probe operating on electrochemical principles is inserted into the medium to read the dissolved oxygen level. Further, optical sensors can be used allowing for fast, continuous measurements. These items may be measured during the manufacturing process to ensure enough oxygen is present in the medium to facilitate the growth of the oleaginous microorganisms.

The dissolved oxygen level in the medium may be greater than about 10%, 20%, 30%, 40%, 50%, 60%, 70%, 80%, or 90% or greater. The dissolved oxygen in the medium may be in a range of about 10% to about 50%. The dissolved oxygen in the medium may be in a range of about 10% to about 20%, about 20% to about 30%, about 30% to about 40%, about 40% to about 50%, about 50% to about 60%, about 60% to about 70%, about 70% to about 80%, or about 80% to about 90%.

In the systems and methods described herein, culturing the oleaginous microorganism in the medium may be done at a temperature range of about 24 to about 33 degrees Celsius. The temperature of the medium may be greater than about 24 degrees Celsius. The temperature of the medium may be at a range of about 10 to about 15 degrees Celsius, about 15 to about 20 degrees Celsius, about 20 to about 25 Celsius, about 25 to about 30 Celsius, about 30 to about 35 Celsius, about 35 to about 40 Celsius, about 40 to about 45 Celsius, about 45 to about 50 Celsius, about 50 to about 55 Celsius, or about 55 to about 60 Celsius. The temperature of the medium may be greater than about 10, 20, 30, 40, 50, or 60 degrees Celsius. The temperature of the medium may be less than about 100, 90, 80, 60, 50, or 40 degrees Celsius.

In certain embodiments, the systems and methods may also comprise measuring a growth rate of the oleaginous microorganism during the manufacturing process. For example, the oil production unit may comprise a growth rate monitoring unit configured to measure the growth rate of the oleaginous microorganisms inside the bioreactor. The growth rate can be measured, for example, by utilizing a specialized micro-titer culture system equipped with an optical sensor used for monitoring cell growth. The growth rate may be greater than 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or 1.0 $h^{-1}$.

In certain embodiments, the systems and methods may also comprise measuring an oil titer in the medium. For example, the oil production unit may further comprise an oil monitoring unit configured to measure an oil titer in the bioreactor while the oleaginous microorganism produces oil. As an example, the oil titer measured may be above about 10 grams of oil per liter of medium. The oil titer may be greater than about 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, or about 400 grams of oil per liter of medium. The oil titer may be measured in a range of about 50 to about 200 grams of oil per liter of medium. The oil titer may be measured in a range of about 10 to about 50, about 50 to about 100, about 100 to about 150, about 150 to about 200, about 200 to about 250, about 250 to about 300, about 300 to about 350, and about 350 to about 400 grams of oil per liter of medium.

In certain embodiments, the systems and methods may also comprise measuring an oil titer in the medium after culturing the oleaginous microorganism for a period of time. In some cases, the oil may have a titer of at least about 5 grams per liter (g/L), 6.0 g/L, 6.5 g/L, 7.0 g/L, 7.5 g/L, 10 g/L, 15 g/L, or more in the medium after culturing the oleaginous microorganism for 75 hrs. In some cases, the oil may have a titer of at most about 15 g/L, 10 g/L, 7.5 g/L, 7.0 g/L, 6.5 g/L, 6.0 g/L, and 5 g/L, or less in the medium after culturing the oleaginous microorganism for 75 hrs. In some cases, the oil may have a titer of at least about 10 grams per liter (g/L) in the medium after culturing the oleaginous microorganism for 75 hrs. In some cases, the oil may have a titer of at least about 5 grams per liter (g/L), 6.0 g/L, 6.5 g/L, 7.0 g/L, 7.5 g/L, 10 g/L, 15 g/L, or more in the medium after culturing the oleaginous microorganism for at least 50 hrs, 60 hrs, 70 hrs, 75 hrs, 80 hrs or more. In some cases, the oil may have a titer of at least about 5 grams per liter (g/L), 6.0 g/L, 6.5 g/L, 7.0 g/L, 7.5 g/L, 10 g/L, 15 g/L, or more in the medium after culturing the oleaginous microorganism for at most 80 hrs, 75 hrs, 70 hrs, 60 hrs, 50 hrs, or less.

In certain embodiments, the systems and methods may also comprise measuring an oil titer in the medium after culturing the oleaginous microoraganism for at least 50 hrs, 100 hrs, 150 hrs, 200 hrs, 250 hrs, 300 hrs, or more. In some cases, the method may include measuring an oil titer in the medium after culturing the oleaginous microoraganism for at most 300 hrs, 250 hrs, 200 hrs, 150 hrs, 100 hrs, 50 hrs, or less. In some cases, the method may include measuring an oil titer in the medium after culturing the oleaginous microoraganism from 50 hrs to 300 hrs, 100 hrs to 300 hrs, 150 hrs to 300 hrs, 200 hrs to 300 hrs, 250 hrs to 300 hrs, 100 hrs to 250 hrs, 150 hrs to 250 hrs, 200 hrs to 250 hrs, or 150 hrs to 200 hrs.

In some cases, the oil may have a titer of at least about 5 grams per liter (g/L), 6.0 g/L, 6.5 g/L, 7.0 g/L, 7.5 g/L, 10 g/L, 15 g/L, 20 g/L, 25 g/L, 30 g/L, 35 g/L, 40 g/L, 45 g/L, 50 g/L, or more in the medium after culturing the oleaginous microorganism for at least 25 hrs, 50 hrs, 75 hrs, 100 hrs, 125 hrs, 150 hrs, 175 hrs, 200 hrs, 225 hrs, 250 hrs, 275 hrs, 300 hrs, or more.

In some cases, the oil may have a titer of at least about 5 grams per liter (g/L), 6.0 g/L, 6.5 g/L, 7.0 g/L, 7.5 g/L, 10 g/L, 15 g/L, 20 g/L, 25 g/L, 30 g/L, 35 g/L, 40 g/L, 45 g/L, 50 g/L, or more in the medium after culturing the oleaginous microorganism for at most 300 hrs, 275 hrs, 250 hrs, 225 hrs, 200 hrs, 175 hrs, 150 hrs, 125 hrs, 100 hrs, 75 hrs, 50 hrs, 25 hrs, or less.

In some cases, the oil may have a titer of at most about 50 g/L, 45 g/L, 40 g/L, 35 g/L, 30 g/L, 25 g/L, 20 g/L, 15 g/L, 10 g/L, 7.5 g/L, 7.0 g/L, 6.5 g/L, 6.0 g/L, 5.0 g/L, or less in the medium after culturing the oleaginous microorganism for at least 25 hrs, 50 hrs, 75 hrs, 100 hrs, 125 hrs, 150 hrs, 175 hrs, 200 hrs, 225 hrs, 250 hrs, 275 hrs, 300 hrs, or more.

In some cases, the oil may have a titer of at most about 50 g/L, 45 g/L, 40 g/L, 35 g/L, 30 g/L, 25 g/L, 20 g/L, 15 g/L, 10 g/L, 7.5 g/L, 7.0 g/L, 6.5 g/L, 6.0 g/L, 5.0 g/L, or less in the medium after culturing the oleaginous microorganism for at most 300 hrs, 275 hrs, 250 hrs, 225 hrs, 200 hrs, 175 hrs, 150 hrs, 125 hrs, 100 hrs, 75 hrs, 50 hrs, 25 hrs, or less.

In some cases, the oil may have a titer of at least about 5 grams per liter (g/L), 6.0 g/L, 6.5 g/L, 7.0 g/L, 7.5 g/L, 10 g/L, 15 g/L, 20 g/L, 25 g/L, 30 g/L, 35 g/L, 40 g/L, 45 g/L, 50 g/L, or more in the medium after culturing the oleaginous microorganism for at least 25 hrs, 50 hrs, 75 hrs, 100 hrs, 125 hrs, 150 hrs, 175 hrs, 200 hrs, 225 hrs, 250 hrs, 275 hrs, 300 hrs, or more. In some cases, the oil may have a titer of at most about 50 g/L, 45 g/L, 40 g/L, 35 g/L, 30 g/L, 25 g/L, 20 g/L, 15 g/L, 10 g/L, 7.5 g/L, 7.0 g/L, 6.5 g/L, 6.0 g/L, 5.0 g/L, or less in the medium after culturing the oleaginous microorganism for at least 25 hrs, 50 hrs, 75 hrs, 100 hrs, 125 hrs, 150 hrs, 175 hrs, 200 hrs, 225 hrs, 250 hrs, 275 hrs, 300 hrs, or more.

In some cases, the oil may have a titer of at least about 10 g/L in the medium after culturing the oleaginous microorganism for 75 hrs. In some cases, the oil may have a titer of at least about 15 g/L in the medium before culturing the oleaginous microorganism for 150 hrs. In some cases, the oil may have a titer of at least about 20 g/L in the medium after culturing the oleaginous microorganism for 150 hrs. In some cases, the oil may have a titer of at least about 25 g/L in the medium before culturing the oleaginous microorganism for 200 hrs. In some cases, the oil may have a titer of at least about 28 g/L in the medium after culturing the oleaginous microorganism for 200 hrs. In some cases, the oil may have a lipid titer of at least about 28 g/L in the medium before culturing the oleaginous microorganism for 250 hrs. In some cases, the oil may have a lipid titer of at least about 28 g/L to 50 g/L of oleaginous microorganism at the time of the harvesting.

In some cases, the oil may have a titer of at least about 10 g/L in the medium after culturing the oleaginous microorganism for 75 hrs. In some cases, the oil may have a titer of at least about 15 g/L in the medium before culturing the oleaginous microorganism for 150 hrs. In some cases, the oil may have a titer of at least about 20 g/L in the medium after culturing the oleaginous microorganism for 150 hrs. In some cases, the oil may have a titer of at least about 25 g/L in the medium before culturing the oleaginous microorganism for 200 hrs. In some cases, the oil may have a titer of at least about 28 g/L in the medium after culturing the oleaginous microorganism for 200 hrs. In some cases, the oil may have a lipid titer of at least about 28 g/L in the medium before culturing the oleaginous microorganism for 250 hrs. In some cases, the oil may have a lipid titer of at least about 28 g/L to 50 g/L of oleaginous microorganism at the time of the harvesting.

In some cases, the oil may have a titer of at most about 10 g/L in the medium after culturing the oleaginous microorganism for 75 hrs. In some cases, the oil may have a titer of at most about 20 g/L in the medium before culturing the oleaginous microorganism for 150 hrs. In some cases, the oil may have a titer of at least about 20 g/L in the medium after culturing the oleaginous microorganism for 150 hrs. In some cases, the oil may have a titer of at most about 30 g/L in the medium before culturing the oleaginous microorganism for 200 hrs. In some cases, the oil may have a titer of at most 35 g/L in the medium after culturing the oleaginous microorganism for 200 hrs. In some cases, the oil may have a lipid titer of at most about 40 g/L in the medium before culturing the oleaginous microorganism for 250 hrs.

In some cases, the oil may have a lipid titer of at least about 28 g/L to 50 g/L of oleaginous microorganism at the time of the harvesting. In some cases, the oil may have a lipid titer of at least about 25 g/L to 40 g/L of oleaginous microorganism at the time of the harvesting. In some cases, the oil may have a lipid titer of at least about 28 g/L to 35 g/L of oleaginous microorganism at the time of the harvesting.

In some embodiments, the oil may have a lipid percentage after culturing the oleaginous microorganism for a period of time. In some cases, the oil may have a lipid percentage of at least about 20%, 30% or 40% of dry cell weight after culturing the oleaginous microorganism for 100 hrs. In some cases, the oil may have a lipid percentage of at least about 20%, 30%, 40%, 50%, or more of dry cell weight after culturing the oleaginous microorganism for 150 hrs. In some cases, the oil may have a lipid percentage of at least about 30%, 40%, 50%, or more of dry cell weight after culturing the oleaginous microorganism for 200 hrs. In some cases, the oil may have a lipid percentage of at least about 40%, 50%, 60%, or more of dry cell weight after culturing the oleaginous microorganism for 250 hrs. In some cases, the oil may have a lipid titer of at least about 40%, 50%, 60%, 65%, or more in the medium after culturing the oleaginous microorganism for 250 hrs.

In some cases, the oil may have a lipid percentage of at least about 20%, 30% or 40% of dry cell weight after culturing the oleaginous microorganism for 100 hrs. In some cases, the oil may have a lipid percentage of at most about 50%, 40%, 30%, 20%, or less of dry cell weight after culturing the oleaginous microorganism for 150 hrs. In some cases, the oil may have a lipid percentage of at most about 50%, 40%, 30%, or less of dry cell weight after culturing the oleaginous microorganism for 200 hrs. In some cases, the oil may have a lipid percentage of at most about 60%, 50%, or less of dry cell weight after culturing the oleaginous microorganism for 250 hrs. In some cases, the oil may have a lipid titer of at most about 65%, 60%, 55%, 50%, 40% or less in the medium after culturing the oleaginous microorganism for 250 hrs.

VI. Harvesting the Oil from the Microorganism

The oil may be harvested from the oleaginous microorganism in a variety of ways. For example, the oil may be centrifuged from the oleaginous microorganism. The oil may also be separated from the oleaginous microorganism through a lysis method comprising an enzymatic, physical, or chemical procedure. The lysis method may comprise shearing the cell membranes of the oleaginous microorganisms with the use of a cell homogenizer. The oil may also be separated using a combination of centrifugation and enzymatic hydrolysis methods. For example, the oleaginous microorganism may be lysed by incubating in the presence of cell wall degrading enzymes, and the resulting lysed cells, released oil, and growth medium are centrifuged in order to separate the lighter oil fraction from the heavier aqueous and solid cellular fractions. The enzymatic hydrolysis can be used to help further free the oil from the oleaginous microorganism. For example, enzymes to be used in the hydrolysis can include those produced from Trichodermi *reesei* or *Arthrobacter* leuteus, and can contain, potentially amongst others, β-1,3 glucanase and β-1,3-glucan laminaripentaohydrolase activities, which hydrolyze glucose polymers at the β-1,3-glucan linkages. Other enzymes that may be used include mannanase, cellulase, b-glucosidase, amylase, invertase, chitinase, protease, and the like.

In embodiments for the co-location of an ethanol production unit and an oil production unit, the oil production unit may comprise an enzymatic hydrolysis reactor, a centrifuge, or a cell homogenizer to perform the separation techniques described herein.

The oil may be harvested from the microorganism when the microorganism comprises the oil at greater than a 50% weight percentage. The oil may be harvested from the microorganism when the microorganism comprises oil at greater than a 20%, 30%, 40%, 50%, 60%, 70%, 80%, or 90% or higher weight percentage at the completion of the culturing process. The oil may be harvested from the microorganism when the microorganism comprises oil at a range of about a 10% to about 40%, 20% to about 50%, 50% to about 70%, or 50% to about 90% weight percentage.

In some embodiments, the oil may be harvested from the oleaginous microorganism when the oil is at least about 10%, 15%, 20%, 25%, 30%, 35%, 40%, 45%, 50%, 55%, 60%, 65%, 70%, or more by weight of the oleaginous microorganism. In some cases, the oil may be harvested from the oleaginous microorganism when the oil is at most about 70%, 65%, 60%, 55%, 50%, 45%, 40%, 35%, 30%, 25%, 20%, 15%, 10%, or less. In some cases, the oil may be harvested from the oleaginous microorganism when the oil is from about 10% to 70%, 20% to 60%, 30% to 60%, 40% to 60%, 40% to 55%, or 45% to 50%.

In some embodiments, at the time of the harvesting (e.g., during step c) the oleaginous microorganism may be present in the medium at a concentration of least 30 g/L, 35 g/L, 40 g/L, 45 g/L, 50 g/L, 75 g/L, or more by dry cell weight. In some cases, at the time of harvesting, the oleaginous microorganism may be present in the medium at a concentration of most 75 g/L, 50 g/L, 45 g/L, 40 g/L, 35 g/L, 30 g/L, 25 g/L, 20 g/L, or less by dry cell weight. In some cases, at the time of harvesting, the oleaginous microorganism may be present in the medium at a concentration 20 g/L to 75 g/L, 30 g/L to 50 g/L, 35 g/L to 45 g/L, 40 g/L to 50 g/L, 20 g/L to 30 g/L, or 35 g/L to 40 g/L by dry cell weight.

In some embodiments, at the time of the harvesting of step c), the lipid titer in the medium may be at least 10 g/L, 15 g/L, 20 g/L 25 g/L, 30 g/L, 35 g/L, or more. In some cases, at the time of the harvesting of step c), the lipid titer in the medium may be at most about 35 g/L, 30 g/L, 25 g/L, 20 g/L, 15 g/L, 10 g/L, or less. In some cases, at the time of the harvesting of step c), the lipid titer in the medium may be from about 10 g/L to 40 g/L, 15 g/L to 35 g/L, 15 g/L to 25 g/L, or 15 g/L to 20 g/L.

In some embodiments, culturing an oleaginous microorganism in a medium and adding ethanol to the medium may be performed in a bioreactor in a fed-batch process. In some embodiments, culturing an oleaginous microorganism in a medium and adding ethanol to the medium may be performed in a bioreactor in a continuous culture process.

In some embodiments, a fed-batch process may be an operational technique where one or more nutrients (e.g., ethanol) are supplied to the bioreactor during cultivation. In some cases, the product(s) (e.g., oil) may remain in the bioreactor until the end of the run. In some cases, all the nutrients may be fed into the bioreactor. The fed-batch process may allow for improved controlling of concentration of nutrients (e.g., ethanol) which may allow for greater yield or productivity of oil. In some cases, a continuous culture process may be used to reproducibly cultivate oleaginous microorganisms such that the culture conditions remain in a state over extended periods of time. The continuous culture process may allow for improved productivity.

In some embodiments, the harvesting yields at least about 0.2 grams of oil per gram of ethanol added in step b). In some cases, the harvesting yields at least about 0.01 g, 0.05 g, 0.1 g, 0.15 g, 0.2 g, 0.25 g, 0.3 g, 0.35 g, 0.4 g, 0.45 g, 0.5 g, or more, per gram of ethanol added in step b). In some cases, the harvesting yields at most about 0.5 g, 0.4 g, 0.35 g, 0.3 g, 0.25 g, 0.2 g, 0.15 g, 0.1 g, 0.05 g, 0.01 g, or less, per gram of ethanol added in step b). In some cases, the harvesting yields at most about 0.01 g to 0.5 g, 0.1 g to 0.5 g, 0.1 g to 0.3 g, 0.15 g to 0.2 g, 0.2 g to 0.3 g, per gram of ethanol added in step b).

VII. Oil Compositions

The oil harvested from the systems and methods described herein may include a polyunsaturated fatty acid content. An unsaturated fatty acid is a fatty acid that contains a carbon-double bond, and that double bond can be in the cis configuration or the trans configuration. A polyunsaturated fatty acid is a fatty acid containing more than one carbon-carbon double bonds. The polyunsaturated fatty acid content may be a percentage relative to the total TAG content of the oil. The polyunsaturated fatty acids (PUFA) content may be less than about 1.0%, 2.0%, 3.0%, 4.0%, or 5.0% The PUFA content may be more than about 0.1%, 0.5%, 1.0%, 1.5%, 2.0%, 2.5%, or 3.0%. The PUFA content may be from about 0.10% to 5.0%, 0.5% to 3.0%, or 1.0% to 2.0%. The PUFA content may be less than 2.0%. In some embodiments, the PUFA content may be below a detection limit or considered negligible. In some cases, the percentage may be relative to a total weight percent. In some cases, there may be no PUFA.

The oil may include monounsaturated fatty acids (MUFA) content. The MUFA content may be a percentage relative to the total TAG content of the oil. The MUFA content may be more than about 40%, 50%, 60%, 70%, 80%, 90% or 95%. The MUFA content may be less than about 95%, 90%, 80%, 70%, 60%, or 55%. The MUFA content may be from about 40% to 95%, 50% to 95%, 50% to 75%, 50% to 55%, 40% to 95%, 50% to 95%, 50% to 75%, 50% to 55%. The MUFA content may be more than about 50%. The MUFA content may be from about 50% to 95%. In some embodiments, the MUFA content may be below a detection limit or considered negligible. In some cases, the percentage may be relative to a total weight percent.

The oil harvested from methods described herein may comprise omega-6 fatty acids content. The omega-6 fatty acids content may be a percentage relative to the total TAG content of the oil. The omega-6 fatty acids content may be present at up to 10% by weight. The oil may comprise omega-6 fatty acids at less than about 9.5%, 9.0%, 8.5%, 8.0%, 7.5%, 7.0%, 6.5%, 6.0%, 5.5%, 5.0%, 4.5%, 4.0%, 3.5%, 3.0%, 2.5%, 2.0%, 1.5%, 1.0%, 0.9%, 0.8%, 0.7%, 0.6%, 0.5%, 0.4%, 0.3%, 0.2%, or about 0.1% by weight. The oil may comprise omega-6 fatty acids at up to 0.1%, 0.2%, 0.3%, 0.4%, 0.5%, 0.6%, 0.7%, 0.8%, 0.9%, 1.0%, 1.5%, 2.0%, 2.5%, 3.0%, 3.5%, 4.0%, 4.5%, 5.0%, 5.5%, 6.0%, 6.5%, 7.0%, 7.5%, 8.0% 8.5%, 9.0%, 9.5% or at most about 10.0% by weight. The omega-6 fatty acid content may be from about 0.2% to 2.0%, 0.2% to 1.0%, 0.2% to 0.5%, or 0.5% to 1.5%. In some embodiments, the omega-6 fatty acids content may be below a detection limit or considered negligible. In some cases, there may be no omega-6 fatty acids content.

The harvested oil may also comprise an oxidative stability index (OSI) which may be used to determine the relative oxidative stability of the fatty materials within the oil. The oxidative stability of the oil may be determined using the American Oil Chemical Society (AOCS) standard method CD 12B-92 and/or the Rancimat method. In some embodiments, the oxidative stability of the oil may be measured isothermally at elevated temperatures to accelerate oxidation. In some cases, the OSI is the point of maximum change of the rate of oxidation. In some cases, the OSI is a method that may determine the relative resistance of fats or oils to oxidation from the oil.

The oil may have an OSI value. The oil OSI value may be determined without the use of external antioxidants in the oil. The oil may have an OSI value of greater than about 30 hrs, 40 hrs, 50 hrs, 60 hrs, 70 hrs, 80 hrs, 90 hrs, 100 hrs, 150 hrs or more. The oil may have an OSI value of less than about 150 hrs, 100 hrs, 90 hrs, 80 hrs, 70 hrs, 60 hrs, 50 hrs, or less. The oil may have an OSI value from about 30 hrs to 200 hrs, 50 hrs to 200 hrs, 50 hrs to 150 hrs, or 50 hrs to 100 hrs.

The oil may also have a $^{13}C/^{12}C$ ratio. As described above for ethanol, the oil too may have a $^{13}C/^{12}C$ ratio similar to that of atmospheric carbon dioxide or plants. The oil may have a $^{13}C/^{12}C$ ratio similar to ethanol produced by fermentation. The $^{13}C/^{12}C$ ratio may be between about −32 to about −6 0/100. The $^{13}C/^{12}C$ ratio may be between about −10 to about 0/100. The $^{13}C/^{12}C$ ratio may be between about −20 to about −10 0/100. The $^{13}C/^{12}C$ ratio may be between about −30 to about −2 0/100. The $^{13}C/^{12}C$ ratio may be between about −40 to about −3 0/100. The $^{13}C/^{12}C$ ratio may be between about −50 to about −4 0/100. The $^{13}C/^{12}C$ ratio may be between about −60 to about −5 0/100. The $^{13}C/^{12}C$ ratio may be between about −70 to about −6 0/100. The $^{13}C/^{12}C$ ratio may be between about −80 to about −70 0/100. The $^{13}C/^{12}C$ ratio may be between about −90 to about −80 0/100. And the $^{13}C/^{12}C$ ratio may be between about −100 to about $-90^{o}/_{100}$. The $^{13}C/^{12}C$ ratio may be less than 0 0/100, −10 0/100, −20 0/100, −30 0/100, −40 0/100, −50 0/100, −60 0/100, −70 0/100, −80 0/100, or −90 0/100 or lower.

The harvested oil may be used as a cooking oil, a salad oil, a fryer oil, etc. The harvested oil may be used in vegan butter, vegan animal fat, palm-free shortening, etc.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

All references cited herein are fully incorporated by reference. Having now fully described the invention, it will be understood by one of skill in the art that the invention may be performed within a wide and equivalent range of conditions, parameters and the like, without affecting the spirit or scope of the invention or any embodiment thereof.

EXAMPLES

Example 1: Determination of the Oil Stability Index Using the AOCS Standard

An OSI method (AOCS Cd12b-92) is performed by passing air through a sample of oil that is kept under high temperature (70-110 degrees Celsius). The air and temperature aids a rapid degradation of the oil, such as a TAG, into volatile organic acids. The air stream flushes the volatile acids and products from the oil into a conductivity cell containing water where they are solubilized. These products, once dissolved in the water solution, disassociate into ions, thus changing the conductivity of the water. A rapid rise in conductivity corresponds to the induction point, which gives the oxidative "failure" of the sample. The time (hours) to the induction point is the OSI time. Oils that are more resistant to oxidative breakdown will have a longer OSI time, while those that are less resistant to oxidative breakdown will have a shorter OSI time.

Example 2: Separating Oil from the Oleaginous Microorganism Using Centrifugation and Enzymatic Hydrolysis Oil is recovered from an oleaginous microorganism by a combined process of cell lysis, to liberate the oil from the cell, and centrifugation, to separate the lighter oil fraction from the heavier aqueous and solid fractions. After fermentation is complete, the pH of the fermentation broth is adjusted to between 6.5 and 7.5 and brought to 35-45 degrees Celsius. A cell wall degrading enzyme cocktail is then added. A cocktail can contain enzymes of commercial origin, such as lyticase or zymolase, or derived directly from the broth of a producing organism, such as Trichodermi *reesei* or *Arthrobacter* leuteus, and will contain, potentially amongst others, β-1,3 glucanase and β-1,3-glucan laminaripentao-hydrolase activities, which hydrolyze glucose polymers at the β-1,3-glucan linkages. Other enzymes that are useful include mannanase, cellulase, b-glucosidase, amylase, invertase, chitinase, protease, and the like. The lysis of these cell wall and carbohydrate polymer linkages results in the breakdown of the cell wall of the oleaginous microorganism, such that the cytoplasm and its contents, including oil, are released into the broth. Other useful enzyme activities include nucleases, and proteases. Lysis of cells is monitored from fractions removed from the reactor microscopically through the formation and lysis of spheroplasts and spectrophotometrically by monitoring the decrease in absorbance at 800 nm. Once lysis is complete, the resulting broth contains a mixture of aqueous medium, cellular debris, and the liberated TAG. The TAG is not directly miscible with water and is of lower density, and it can be separated from the heavier aqueous and solid fractions by centrifugation. The broth is centrifuged, for example through a continuous disc stack centrifuge, such that the light oil phase is separated from the heavier water and solid phases. This can be accomplished by passing the broth through the centrifuge a single time, or by passing the oil through more than one time, optionally washing the recovered oil with an aqueous solution between each pass. Recovery can be improved by the addition of enzymes to further break down the cellular debris, for example by the addition of one or more nucleases or proteases, such as DNAase, RNase, and proteinase K or the like, to the lysed broth and incubated before centrifugal separation.

Example 3: The Oil Production Process

An oleaginous microorganism, such as *C. oleaginosus* (for example ATCC 20509), is cultivated in an Erlenmeyer flask containing YPD media broth (10 g $L^{-1}$ yeast extract, 20 g $L^{-1}$ peptone, and 20 g $L^{-1}$ glucose) that is incubated in a rotary shaker at 28 degrees Celsius and 100-200 rpm for 2 days until the OD at 600 nm of the inoculum is between 25 and 40. This is then used to inoculate stirred bioreactors at an initial OD at 600 nm of around 0.5.

Stirred Bioreactors

The stirred bioreactors are charged with a base medium composed of 0.05 g $L^{-1}$ $NH_4Cl$, 2.4 g $L^{-1}$ $KH_2PO_4$, 0.9 g $L^{-1}$ $Na_2HPO_4$-12$H_2O$, 1.5 g $L^{-1}$ $MgSO_4$-7$H_2O$, 0.025 g $L^{-1}$ $FeCl_3$-6$H_2O$, 0.001 g $L^{-1}$ $ZnSO_4$-7$H_2O$, 0.2 g $L^{-1}$ $CaCl_2$)-2$H_2O$, 0.024 g $L^{-1}$ $MnSO_4$-5$H_2O$, 0.025 g $L^{-1}$ $CuSO_4$-5$H_2O$, and 0.003 g $L^{-1}$ $Co(NO_3)_2$-6$H_2O$, 30.0 g $L^{-1}$ glucose, 0.5 g $L^{-1}$ yeast extract, and 5.0 g $L^{-1}$ Peptone. The reactors are maintained at 28 degrees Celsius and at a pH of 5.5-6.5 with 70%-100% acetic acid and 3M NaOH. Upon depletion of the initial glucose, carbon source containing Ethanol is fed to maintain a target reactor concentration of Ethanol of 4-30 g/L. Dissolved oxygen is maintained at 30-50% with agitation (up to 800 rpm) and sparging (1.5-8 vvm), oxygen content of air (21-100%), and backpressure (1.2-1.5 bar) as needed. Foam is controlled with antifoam additions (0.01%) bursts as needed. Once the reactors reach capacity from the feeding, the feeding is stopped to allow the remaining carbon source to be consumed, and the resulting culture is prepared for harvest. Samples from the fermentation are collected over the course of the fermentation and monitored for biomass and lipid (TAG) accumulation. These fermentations typically support total biomass concentrations of 30-200 g-DCW/L of biomass in which the biomass is 40-90% lipid.

Example 4: Ethanol as Carbon Source for Lipid Production from Oleaginous Yeast Inoculum preparation: for inoculum preparation, a −20° C. working stock was prepared by culturing cells from a single colony pitched to liquid YPD medium (20 g/L glucose, 20 g/L peptone, 10 g/L yeast extract) incubated at 28° C. with 180 rpm orbital agitation during 48 h. After growth, cells were collected by centrifugation (4000 rpm, 15 minutes), resuspended in fresh YPD medium to achieve a cellular concentration ~$2\times10^9$ cells/mL (verified by Neubauer chamber cell count), and mixed with sterile glycerol at a glycerol:cell stock proportion of 1:1 (v/v), aiming at a final cellular concentration of ~$1\times10^9$ cells/mL in the −20° C. working cell bank.

For inoculum growth, cells from the −20° C. stock were pitched to sterile YPD aiming for an initial cellular concentration of $1\times10^7$ cells/mL in sterile baffled shake flasks, using a medium to shake flask volume proportion of 1:5. Cells were incubated at 28° C. and 180 rpm and collected after ~43 h (at the end of exponential growth phase) for pitching.

Biomass growth was accompanied by measure of OD (Abs 600 nm), converted to dry cell weight (DCW) using an OD vs. DCW calibration curve. For lipid analysis, acid hydrolysis of biomass was conducted using HCl [4M], followed by methanol:chloroform extraction and quantification of lipid content in the dried chloroform fraction by gravimetry. The obtained oils were derivatized with acidified methanol and the subsequent FAMEs were extracted with hexane, which was injected in GC-FID for composition analysis. Carbon sources were analyzed by HPLC

Example 4: Shake Flask Fermentations

Strains tested: *Lipomyces kononenkoae* (L.k.), *Lipomyces tetrasporus* (L.t.), and *Cutaneotrichosporon oleaginosus* (C.o.)

Preliminary tests were done with flasks to gather useful information for the bioreactor runs. The first experiments were performed to evaluate if the selected strains were able to grow and accumulate lipids using ethanol as carbon source or in a combination of glucose and ethanol. At the same time, the tolerance of the yeasts to ethanol was assessed by testing the use of different concentrations of ethanol. These experiments demonstrated that those yeasts can grow and accumulate lipids using ethanol as carbon source. It was demonstrated on C.o. that it can grow and accumulate lipids using ethanol as the only carbon source.

The lipid accumulation on ethanol is higher than on glucose while the growth is a bit lower. Based on these results, ethanol is a surprisingly good feed to support lipid production.

With C.o. it was reached 59.7% lipid content of the dry cell weight on ethanol alone (15 g/L). The different growth conditions and data obtained for C.o. cultivation can be seen in Table 1 below and in FIG. 1.

TABLE 1

Cultivation conditions for C.o.

| | Media | Initial conditions | Duration |
|---|---|---|---|
| Glucose | 30 g/L glucose<br>0.5 g/L yeast extract<br>Basal medium* | Initial OD 0.5<br>180 rpm<br>28° C.<br>pH 5.5 | 5 days |
| Ethanol 30 | 30 g/L ethanol<br>0.5 g/L yeast extract<br>Basal medium* | Initial OD 0.5<br>180 rpm<br>28° C.<br>pH 5.5 | 5 days |
| Ethanol 15 | 15 g/L ethanol<br>0.5 g/L yeast extract<br>Basal medium* | Initial OD 0.5<br>180 rpm<br>28° C.<br>pH 5.5 | 5 days |
| Ethanol 4 | 4 g/L ethanol<br>0.5 g/L yeast extract<br>Basal medium* | Initial OD 0.5<br>180 rpm<br>28° C.<br>pH 5.5 | 5 days |
| G + E (glucose plus ethanol) | 30 g/L glucose<br>4 g/L ethanol<br>0.5 g/L yeast extract<br>Basal medium* | Initial OD 0.5<br>180 rpm<br>28° C.<br>pH 5.5 | 5 days |

*0.05 g/L $NH_4Cl$, 2.4 g/L $KH_2PO_4$, 0.9 g/L $Na_2HPO_4•12H_2O$, 1.5 g/L MgSO4•$7H_2O$, 0.025 g/L $FeCl_3•6H_2O$, 0.001 g/L $ZnSO_4•7H_2O$, 0.2 g/L $CaCl_2•2H_2O$, 0.024 g/L $MnSO_4•5H_2O$, 0.025 g/L $CuSO_4•5H_2O$, 0.003 g/L $Co(NO_3)_2•6H_2O$

Figure 2A:
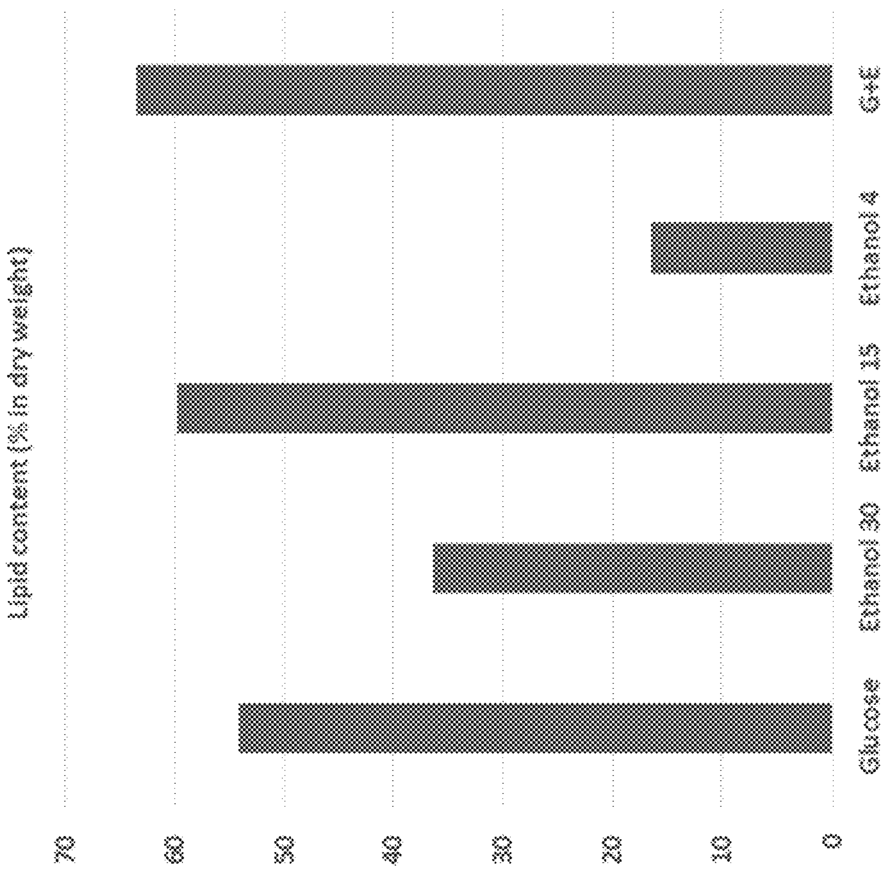
FIG. 2A illustrates lipid content in % dry weight of *Cutaneotrichosporon oleaginosus* in ethanol with various cultivation conditions.
Figure 2B:
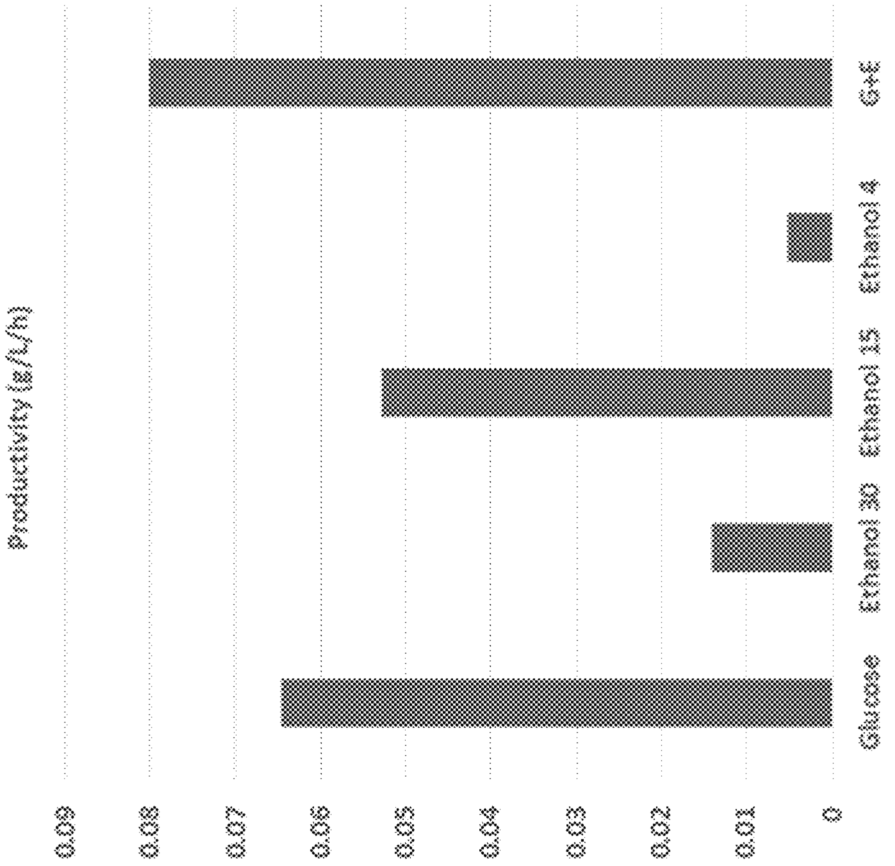
FIG. 2B illustrates productivity of *Cutaneotrichosporon oleaginosus* in ethanol with various cultivation conditions.

FIG. 1 shows the growth curves of C.o. in the various conditions shown in Table 1. FIG. 2A shows the lipid content of the C.o. cultures upon harvesting at the 120 hour timepoint. FIG. 2B shows the average productivity of each of the C.o. cultures.

Example 5: Fed-Batch in Flask Experiment

Baffled flasks were used and a two-stage strategy was implemented by having a first stage for growth with a mix of glucose and ethanol and a second stage for lipid accumulation where ethanol was feed and the only carbon source. *Lipomyces tetrasporus* (L.t.) was used for these experiments and it was possible to reach 33.9 g/L of biomass, 54.3% of lipid content (dry cell weight) and a lipid titer of 17.6 g/L. The growth conditions and data obtained can be seen below in Table 2 and FIG. 3.

TABLE 2

Cultivation conditions

| | Media | Initial conditions | Fed | Duration |
|---|---|---|---|---|
| Fed C 2 | 40 g/L glucose<br>2.5 g/L peptone<br>0.5 g/L yeast extract<br>5 g/L ethanol<br>Basal medium | OD 0.5<br>180 rpm<br>28° C.<br>ipH 5.5 | Start at 51 hours with 2.2 g/L of ethanol, increase to 3.5 on day 4 and to 4.5 at day 5 | 5 Days |

Basal medium: 0.05 g/L $NH_4Cl$, 2.4 g/L $KH_2PO_4$, 0.9 g/L $Na_2HPO_4•12H_2O$, 1.5 g/L MgSO4•$7H_2O$, 0.025 g/L $FeCl_3•6H_2O$, 0.001 g/L $ZnSO_4•7H_2O$, 0.2 g/L $CaCl_2•2H_2O$, 0.024 g/L $MnSO_4•5H_2O$, 0.025 g/L $CuSO_4•5H_2O$, 0.003 g/L $Co(NO_3)_2•6H_2O$.

Figure 3:
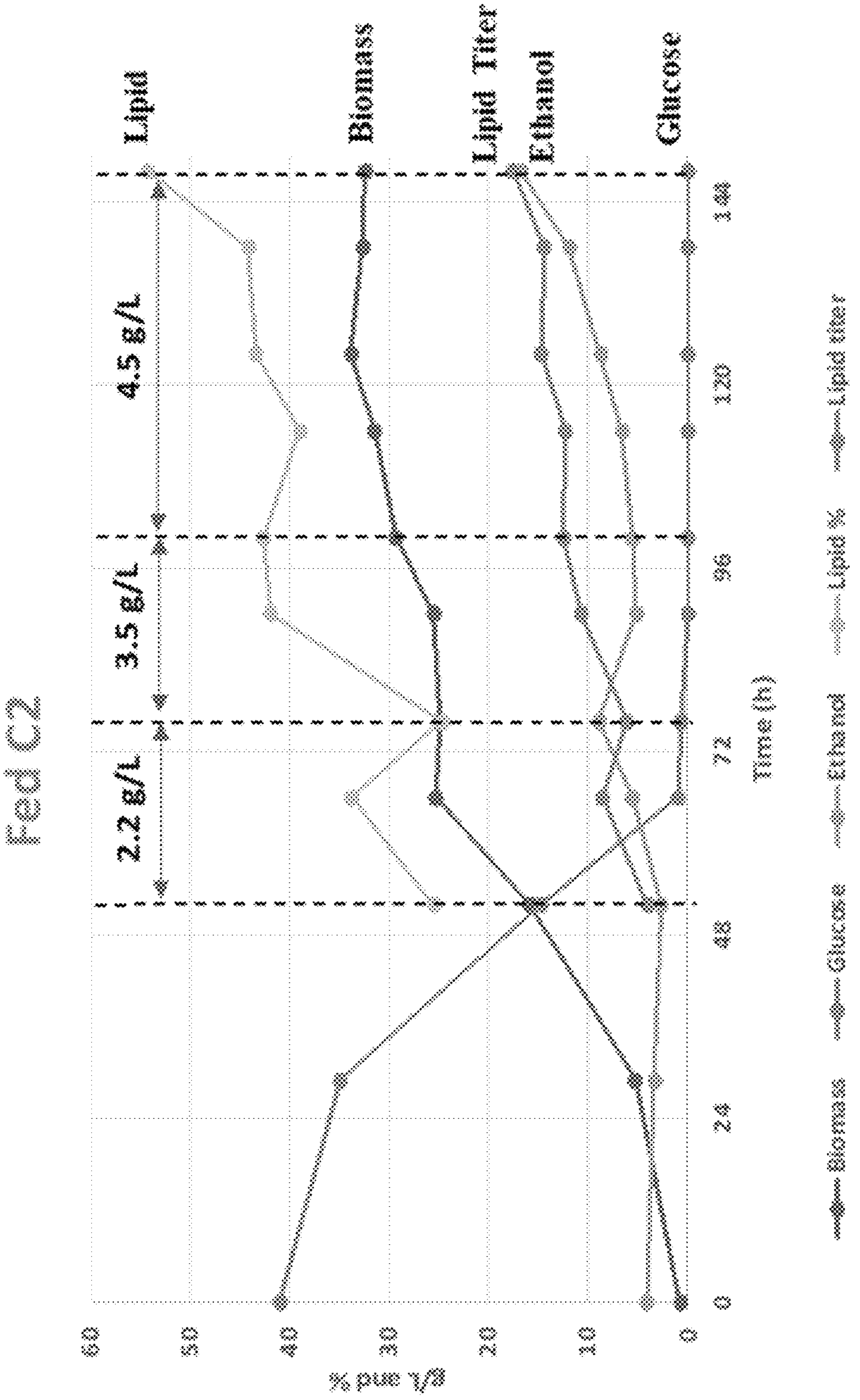
FIG. 3 illustrates two stage batch conditions for *Lipomyces tetrasporus* (L.t.).
Figure 5:
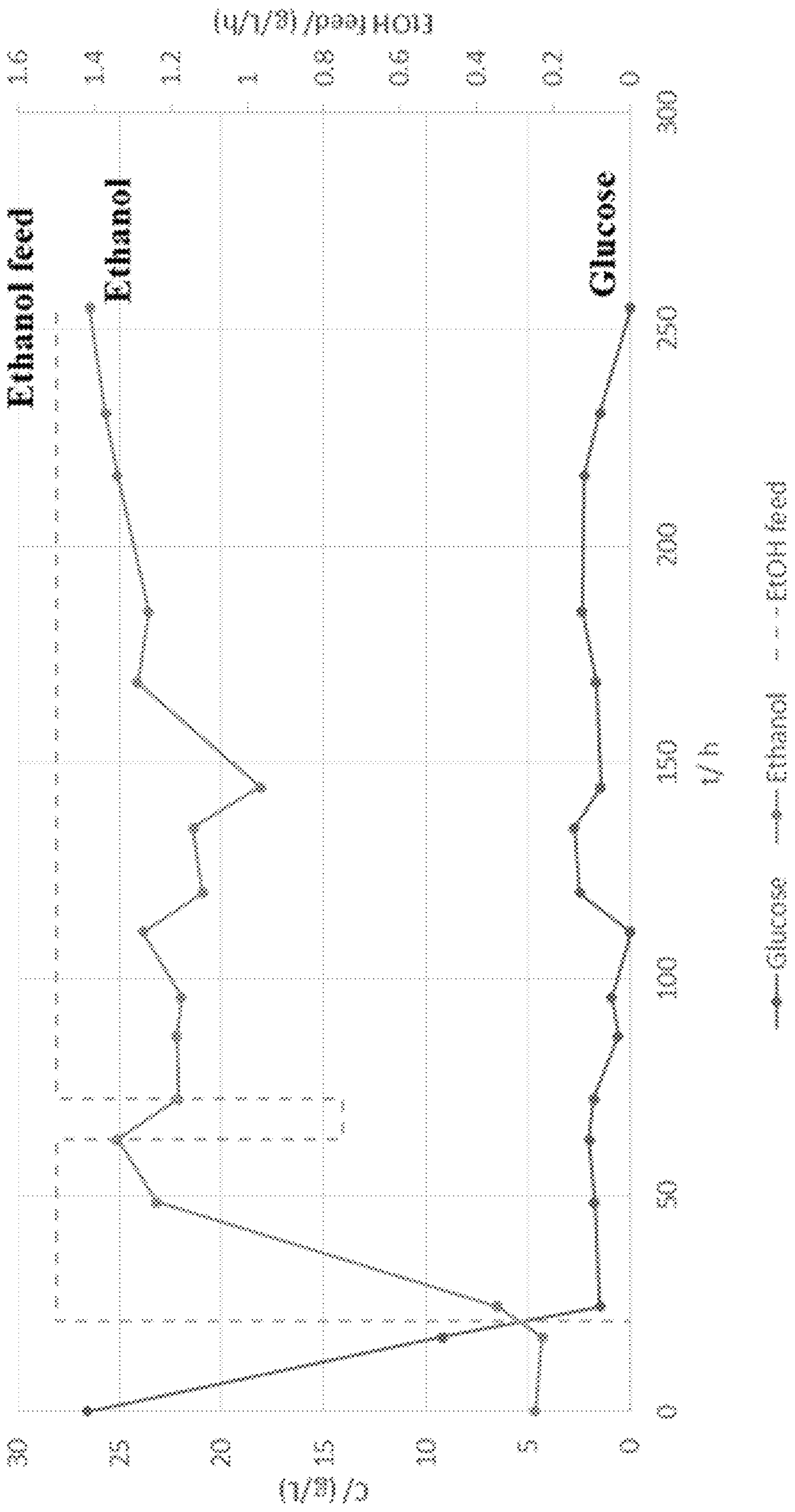
FIG. 5 illustrates carbon source concentration throughout time in *C. oleaginosus* fed-batch fermentation with ethanol feeding.

FIG. 3 shows the growth curve for biomass (g/L) and lipid titer (g/L), along with the concentrations of glucose and ethanol (g/L), along with the lipid percentage with respect to dry cell weight. As shown in FIG. 5, after glucose has been completely consumed, ethanol supports excellent lipid production as the sole carbon source, resulting in a doubling of the lipid concentration from 25 to 55 g/L reaching over 50% of the cellular biomass as lipid.

Example 6: Bioreactor Fermentations with Ethanol Fed-Batch

Bioreactor fermentation methodology: fermentations were conducted in 3 L bioreactors (RALF2, BioEngineering), with 1.5 L of starting volume of the following medium: 0.5 g/L yeast extract, 5 g/L peptone, 0.05 g/L $NH_4Cl$, 2.4 g/L $KH_2PO_4$, 0.9 g/L $Na_2HPO_4.12H_2O$, 1.5 g/L $MgSO_4.7H_2O$, 0.025 g/L $FeCl_3.6H_2O$, 0.001 g/L $ZnSO_4.7H_2O$, 0.2 g/L $CaCl_2).{}_2H_2O$, 0.024 g/L $MnSO_4.5H_2O$, 0.025 g/L $CuSO_4.5H_2O$, 0.003 g/L $Co(NO_3)_2.6H_2O$ and 40 g/L of initial glucose.

For pitching, cellular concentration in the pre-culture was verified by Neubauer chamber cell count to determine the necessary volume to inoculate the bioreactor with an initial cellular concentration of $3\times10^7$ cells/mL. Cells in the corresponding volume were collected by centrifugation (4000 rpm, 15'), resuspended in fermentation medium and pitched in the bioreactor under aseptic conditions. Fermentation parameters were the following: temperature of 28° C., pH fixed at 5.5 controlled with NaOH [5M] and HCl [5M] and dissolved oxygen >50%, controlled by an agitation cascade (between 500 and 800 rpm) maintaining aeration flow rate constant at 1 vvm. Fermentations were conducted in fed-batch configuration, comprising an initial growth phase from glucose in batch followed by feeding with absolute ethanol, initiated upon glucose depletion, with varying flow rates to control ethanol accumulation.

Figure 4:
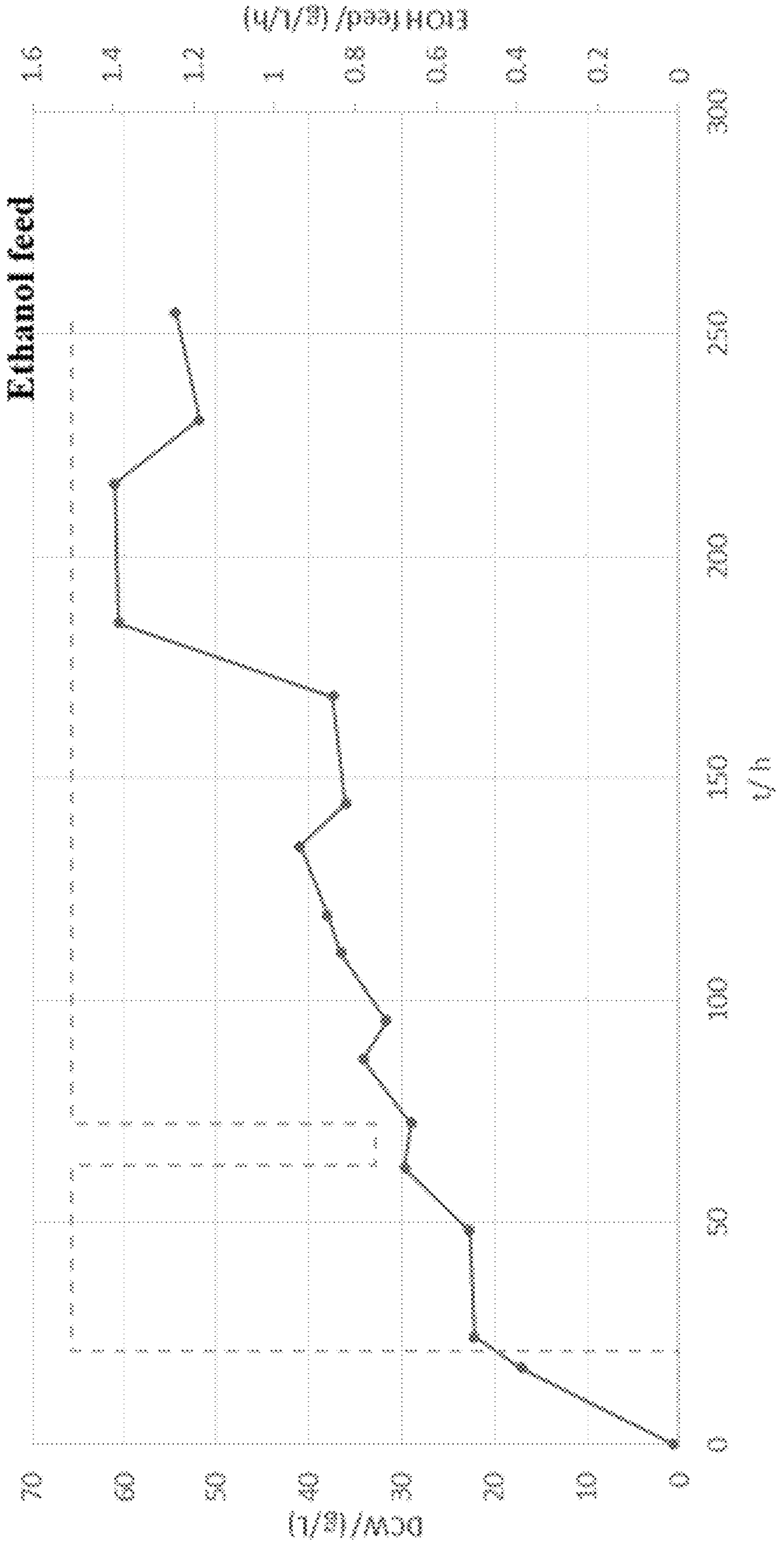
FIG. 4 illustrates biomass growth profile (expressed as DCW from OD) in C. oleaginosus fed-batch fermentation with ethanol feeding.
Figure 6B:
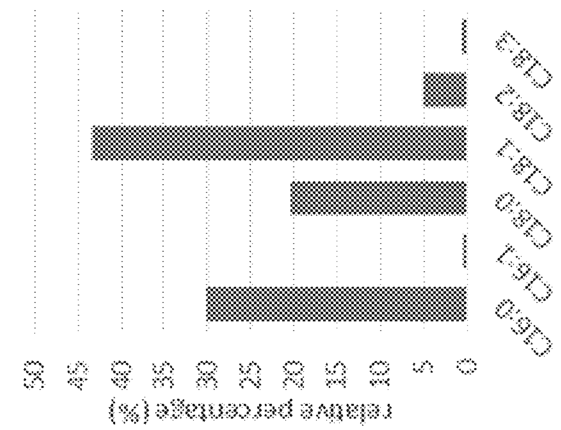
FIG. 6B illustrates fatty acid composition in *C. oleaginosus* fed-batch fermentation with ethanol feeding.
Figure 6A:
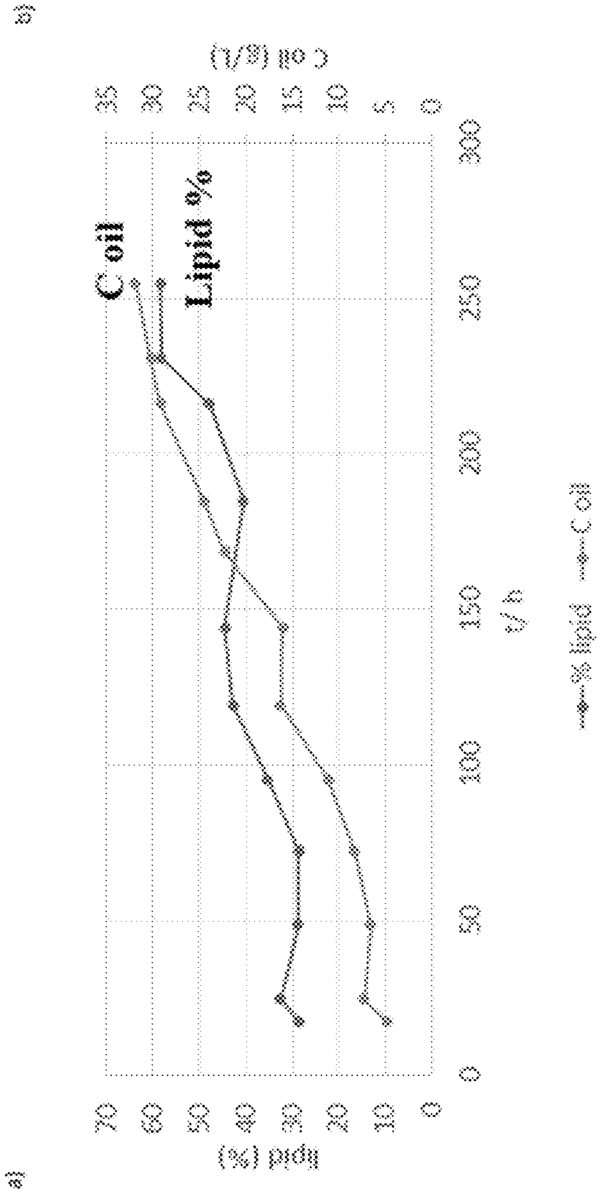
FIG. 6A illustrates lipid titer and percentage throughout time in *C. oleaginosus* fed-batch fermentation with ethanol feeding.

*Cutaneotrichosporon oleaginosus*: The following results were obtained with *C. oleaginosus*. Biomass growth kinetics can be found in FIG. 4, carbon source consumption profiles can be found FIG. 5, and lipid production and composition in FIG. 6A and FIG. 6B. FIG. 6A shows the lipid content as a percentage of dry cell weight ("lipid %") and the concentration of lipids in the culture in grams per liter ("C oil"). Overall, fermentation of *C. oleaginosus* with ethanol feeding achieved a biomass concentration of about 54 g/L with 58% lipid content accounting for a titer near 32 g/L. Ethanol concentrations were surprisingly well tolerated from 5 to over 25 g/L, made up 50 to over 90% of the carbon source during most of the lipid production phase, and supported an increase in lipid titer from 10 g/L to over 30 g/L. These data clearly show that Ethanol may be a surprisingly good carbon source to support lipid production.

Figure 7:
FIG. 7 illustrates biomass growth profile (expressed as DCW from OD) in *L. tetrasporus* fed-batch fermentation with ethanol feeding.
Figure 8:
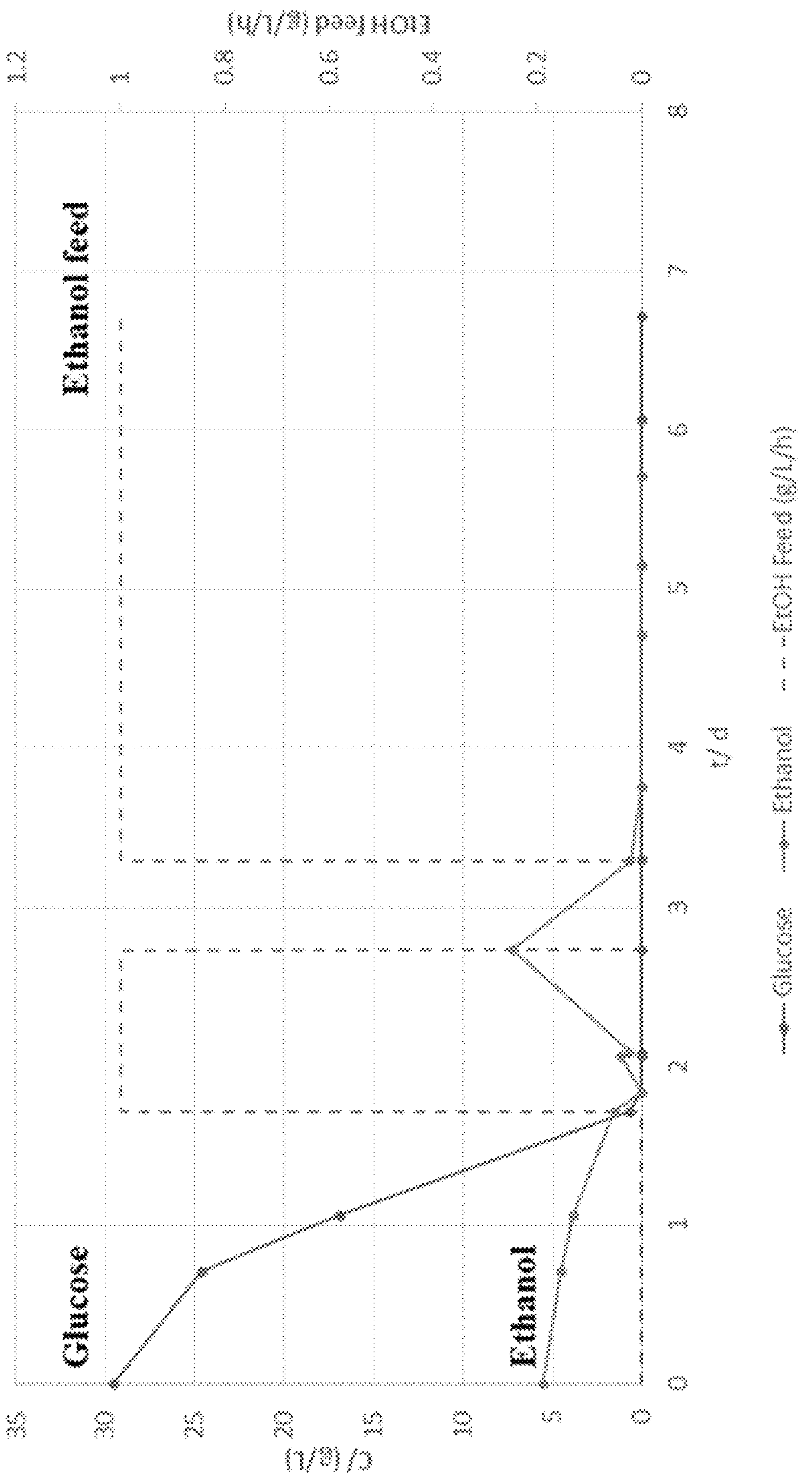
FIG. 8 illustrates carbon source concentration throughout time in *L. tetrasporus* fed-batch fermentation with ethanol feeding.
Figure 9B:
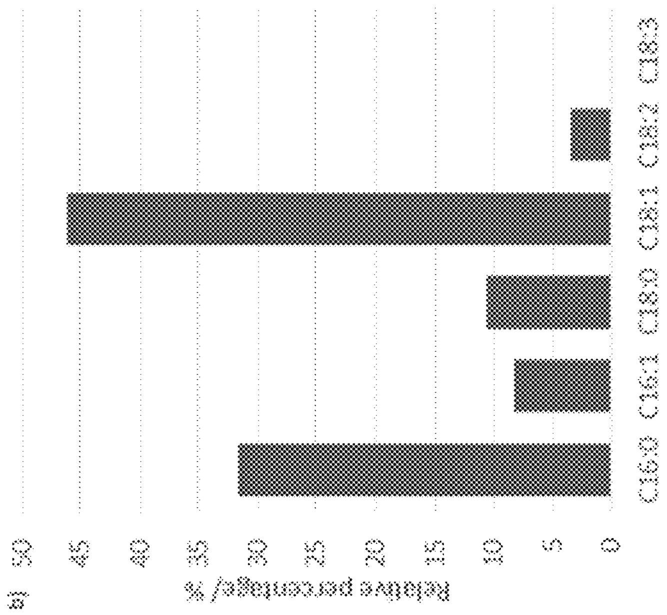
FIG. 9B illustrates fatty acid composition in *L. tetrasporus* fed-batch fermentation with ethanol feeding.
Figure 9A:
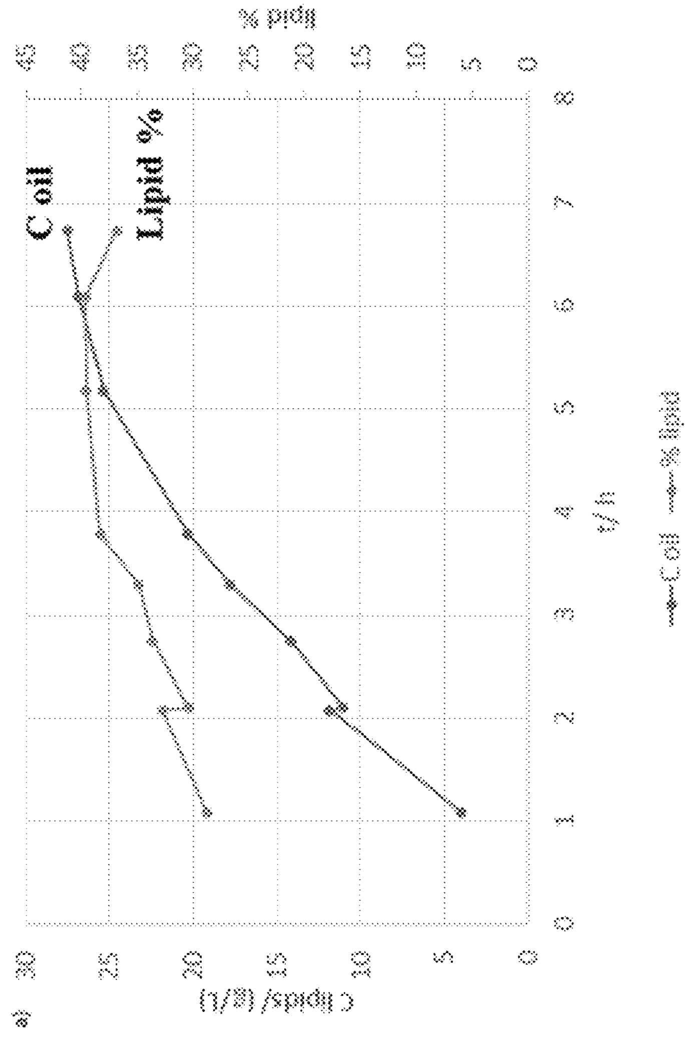
FIG. 9A illustrates lipid titer and percentage throughout time in *L. tetrasporus* fed-batch fermentation with ethanol feeding.

*Lipomyces tetrasporus*: The following results were obtained with *L. tetrasporus*. Biomass growth kinetics can be found in FIG. 7, carbon source consumption profiles can be found in FIG. 8, and lipid production and composition in FIG. 9A and FIG. 9B. FIG. 9A shows the lipid content as a percentage of dry cell weight ("lipid %") and the concentration of lipids in the culture in grams per liter ("C lipids"). Overall, fermentation of L. tetrasporus with ethanol feeding achieved a biomass concentration of about 75 g/L with 37% lipid content accounting for a titer near 28 g/L.

To highlight that even with dissimilar biomass growth and % lipid in the biomass, similar lipid titers were achieved with the two yeast species grown on ethanol, *C. oleaginosus* achieved near 32 g/L, whereas L. tetrasporus achieved near 28 g/L of lipids. Interestingly, both of these divergent oleaginous microorganisms surprisingly utilize ethanol very well as a sole carbon or predominant carbon source for producing lipids. As shown in FIGS. 8B and 11B, these strains under the high ethanol carbon source conditions also produce oils with a majority of oleic acid and less than 5% linoleic acid or other polyunsaturated fatty acids.

What is claimed is:

1. A method of manufacturing an oil comprising a triacylglyceride, the method comprising:

a) providing an oleaginous microorganism;

b) culturing the oleaginous microorganism under glucose depleted conditions in a medium comprising a carbon source as a primary feedstock for lipogenesis, wherein the carbon source during lipogenesis comprises ethanol at greater than 50% by weight, wherein the oleaginous microorganism comprises *Cutaneosporon oleaginosus, Lipomyces tetrasporus, Rhodotorula toluroides*, or *Yarrowia lipolytica*; and c) harvesting the oil from the oleaginous microorganism when the oil is at least 25% by weight of the oleaginous microorganism.

2. The method of claim 1, further comprising fermenting the oleaginous microorganism in an initial growth stage prior to lipogenesis using glucose.

3. The method of claim 1, wherein the ethanol is present in the medium during lipogenesis at a concentration of greater than 0.1%.

4. The method of claim 1, wherein the oil comprises less than 7% omega-6 fatty acids by weight.

5. The method of claim 1, wherein the oil comprises up to 7% omega-6 fatty acids by weight.

6. The method of claim 1, wherein the oil has an oxidative stability index greater than 50 hours.

7. The method of claim 1, wherein the ethanol is cellulosic ethanol.

8. The method of claim 1, wherein the ethanol comprises a $^{13}C/^{12}C$ ratio from about −32 to about −6.

9. The method of claim 1, wherein the oil comprises a $^{13}C/^{12}C$ ratio from about −32 to about −6.

10. The method of claim 1, further comprising, before step (b), sourcing the ethanol from an ethanol manufacturing facility.

11. The method of claim 10, further comprising, distilling the ethanol in a distillation column at the ethanol manufacturing facility and extracting the ethanol from a distillation column outlet.

12. The method of claim 1, further comprising co-manufacturing ethanol alongside the oil at an oil manufacturing facility.

13. The method of claim 1, wherein culturing the oleaginous microorganism in step (b) further comprises the use of an acid to maintain a desired pH.

14. The method of claim 1, wherein culturing the oleaginous microorganism in step (b) further comprises the use of a base to maintain a desired pH.

15. The method of claim 1, further comprising, simultaneous to steps (a)-(c), measuring a dissolved oxygen level during the process.

16. The method of claim 1, further comprising, simultaneous to steps (a)-(c), measuring a dissolved oxygen level in the medium.

* * * * *